(12) United States Patent
Thompson-Nauman et al.

(10) Patent No.: US 12,623,071 B2
(45) Date of Patent: May 12, 2026

(54) SUBSTERNAL ELECTRICAL STIMULATION SYSTEM

(71) Applicant: Medtronic, Inc., Minneapolis, MN (US)

(72) Inventors: Amy E. Thompson-Nauman, Ham Lake, MN (US); Melissa G.T. Christie, Andover, MN (US); Rick D. McVenes, Isanti, MN (US)

(73) Assignee: Medtronic, Inc., Minneapolis, MN (US)

( * ) Notice: Subject to any disclaimer, the term of this patent is extended or adjusted under 35 U.S.C. 154(b) by 443 days.

(21) Appl. No.: 17/661,150

(22) Filed: Apr. 28, 2022

(65) Prior Publication Data

US 2022/0249835 A1     Aug. 11, 2022

Related U.S. Application Data

(60) Continuation of application No. 16/725,458, filed on Dec. 23, 2019, now Pat. No. 11,344,720, which is a
(Continued)

(51) Int. Cl.
*A61N 1/05*          (2006.01)
*A61N 1/365*        (2006.01)
(Continued)

(52) U.S. Cl.
CPC ............. *A61N 1/0587* (2013.01); *A61N 1/05* (2013.01); *A61N 1/365* (2013.01);
(Continued)

(58) Field of Classification Search
CPC ........ A61N 1/0587; A61N 1/05; A61N 1/365; A61N 1/37288; A61N 1/3756; A61N 1/0504
See application file for complete search history.

(56) References Cited

U.S. PATENT DOCUMENTS 3,614,954 A     10/1971     Mirowski et al.
3,706,313 A     12/1972     Milani et al.
(Continued)

FOREIGN PATENT DOCUMENTS

CN          1859870 A     11/2006
CN        102858403 A       1/2013
(Continued)

OTHER PUBLICATIONS

"Emblem S-ICD, Emblem MRI S-ICD," Boston Scientific, REF 4209, A219, Manual 359481-001, Nov. 2015, 72 pp.
(Continued)

*Primary Examiner* — Mark W. Bockelman
(74) *Attorney, Agent, or Firm* — Shumaker & Sieffert, P.A.

(57)          ABSTRACT

Implantable cardiac pacing systems and methods for providing substernal pacing are described. In one example, a cardiac pacing system includes a pacemaker implanted in a patient and an implantable medical electrical lead. The implantable medical electrical lead includes an elongated lead body having a proximal end and a distal portion, a connector configured to couple to the pacemaker at the proximal end of the elongated lead body, and one or more electrodes along the distal portion of the elongated lead body, wherein the distal portion of the elongated lead body of the lead is implanted substantially within an anterior mediastinum of the patient and the pacemaker is configured to deliver pacing pulses to a heart of the patient.

17 Claims, 11 Drawing Sheets

Related U.S. Application Data division of application No. 14/261,479, filed on Apr. 25, 2014, now Pat. No. 10,532,203.

(60) Provisional application No. 61/820,033, filed on May 6, 2013.

(51) Int. Cl.
    *A61N 1/372*     (2006.01)
    *A61N 1/375*     (2006.01)

(52) U.S. Cl.
    CPC ....... *A61N 1/37288* (2013.01); *A61N 1/3756* (2013.01); *A61N 1/0504* (2013.01)

(56) References Cited

U.S. PATENT DOCUMENTS

| | | | | |
|---|---|---|---|---|
| 4,030,509 A | 6/1977 | Heilman et al. | | |
| 4,146,037 A | 3/1979 | Flynn et al. | | |
| 4,183,249 A | * 1/1980 | Anderson | ............... | A61B 8/00 |
| | | | | 73/641 |
| 4,270,549 A | 6/1981 | Heilman | | |
| 4,280,510 A | 7/1981 | O'Neill | | |
| 4,291,707 A | 9/1981 | Heilman et al. | | |
| 4,437,475 A | 3/1984 | White | | |
| 4,450,527 A | 5/1984 | Sramek | | |
| 4,512,351 A | 4/1985 | Pohndorf | | |
| 4,538,624 A | 9/1985 | Tarjan | | |
| 4,669,473 A | 6/1987 | Richards et al. | | |
| 4,693,253 A | 9/1987 | Adams | | |
| 4,708,145 A | 11/1987 | Tacker, Jr. et al. | | |
| 4,765,341 A | 8/1988 | Mower et al. | | |
| 4,787,389 A | 11/1988 | Tarjan | | |
| 4,832,687 A | 5/1989 | Smith, III | | |
| 4,865,037 A | 9/1989 | Chin et al. | | |
| 4,953,551 A | 9/1990 | Mehra et al. | | |
| 5,036,854 A | 8/1991 | Schollmeyer et al. | | |
| 5,099,838 A | 3/1992 | Bardy | | |
| 5,105,810 A | 4/1992 | Collins et al. | | |
| 5,113,869 A | 5/1992 | Nappholz et al. | | |
| 5,125,904 A | 6/1992 | Lee | | |
| 5,129,392 A | 7/1992 | Bardy et al. | | |
| 5,176,135 A | 1/1993 | Fain et al. | | |
| 5,193,539 A | 3/1993 | Schulman et al. | | |
| 5,193,540 A | 3/1993 | Schulman et al. | | |
| 5,203,348 A | 4/1993 | Dahl et al. | | |
| 5,255,691 A | 10/1993 | Otten | | |
| 5,255,692 A | 10/1993 | Neubauer et al. | | |
| 5,261,400 A | 11/1993 | Bardy | | |
| 5,273,053 A | 12/1993 | Pohndorf | | |
| 5,292,338 A | 3/1994 | Bardy | | |
| 5,300,106 A | 4/1994 | Dahl et al. | | |
| 5,312,355 A | 5/1994 | Lee | | |
| 5,331,966 A | 7/1994 | Bennett et al. | | |
| 5,336,252 A | 8/1994 | Cohen | | |
| 5,342,407 A | 8/1994 | Dahl et al. | | |
| 5,366,496 A | 11/1994 | Dahl et al. | | |
| 5,376,105 A | 12/1994 | Hedberg | | |
| 5,385,574 A | 1/1995 | Hauser et al. | | |
| 5,411,539 A | 5/1995 | Neisz | | |
| 5,423,326 A | 6/1995 | Wang et al. | | |
| 5,439,484 A | 8/1995 | Mehra | | |
| 5,441,504 A | 8/1995 | Pohndorf et al. | | |
| 5,456,699 A | 10/1995 | Armstrong | | |
| 5,468,254 A | 11/1995 | Hahn et al. | | |
| 5,476,493 A | 12/1995 | Muff | | |
| 5,509,924 A | 4/1996 | Paspa et al. | | |
| 5,534,018 A | 7/1996 | Wahlstrand et al. | | |
| 5,534,022 A | 7/1996 | Hoffmann et al. | | |
| 5,601,607 A | 2/1997 | Adams | | |
| 5,603,732 A | 2/1997 | Dahl et al. | | |
| 5,613,953 A | 3/1997 | Pohndorf | | |
| 5,690,648 A | 11/1997 | Fogarty et al. | | |
| 5,721,597 A | 2/1998 | Kakinuma et al. | | |
| 5,800,465 A | 9/1998 | Woods et al. | | |
| 5,814,076 A | * 9/1998 | Brownlee | ............ | A61N 1/3704 |
| | | | | 607/9 |
| 5,944,732 A | 8/1999 | Raulerson et al. | | |
| 5,951,518 A | 9/1999 | Licata et al. | | |
| 5,951,593 A | 9/1999 | Lu et al. | | |
| 6,032,079 A | 2/2000 | Ken Knight et al. | | |
| 6,040,082 A | 3/2000 | Haas et al. | | |
| 6,059,750 A | 5/2000 | Fogarty | | |
| 6,091,989 A | 7/2000 | Swerdlow et al. | | |
| 6,095,987 A | 8/2000 | Shmulewitz et al. | | |
| 6,104,957 A | 8/2000 | Ala et al. | | |
| 6,120,431 A | 9/2000 | Magovern | | |
| 6,122,552 A | 9/2000 | Tockman et al. | | |
| 6,129,431 A | 10/2000 | Hansen, Jr. et al. | | |
| 6,159,198 A | 12/2000 | Gardeski et al. | | |
| 6,228,052 B1 | 5/2001 | Pohndorf | | |
| 6,324,414 B1 | 11/2001 | Gibbons et al. | | |
| 6,415,187 B1 | 7/2002 | Kuzma et al. | | |
| 6,445,954 B1 | 9/2002 | Olive et al. | | |
| 6,544,247 B1 | 4/2003 | Gardeski et al. | | |
| 6,721,597 B1 | 4/2004 | Bardy et al. | | |
| 6,730,083 B2 | 5/2004 | Freigang et al. | | |
| 6,733,500 B2 | 5/2004 | Kelley et al. | | |
| 6,749,574 B2 | 6/2004 | O'Keefe | | |
| 6,770,070 B1 | 8/2004 | Balbierz | | |
| 6,772,014 B2 | 8/2004 | Coe et al. | | |
| 6,836,687 B2 | 12/2004 | Kelley et al. | | |
| 6,856,835 B2 | 2/2005 | Bardy et al. | | |
| 6,866,044 B2 | 3/2005 | Bardy et al. | | |
| 6,868,291 B1 | 3/2005 | Bonner et al. | | |
| 6,887,229 B1 | 5/2005 | Kurth | | |
| 6,890,295 B2 | 5/2005 | Michels et al. | | |
| 6,999,819 B2 | 2/2006 | Swoyer et al. | | |
| 7,033,326 B1 | 4/2006 | Pianca et al. | | |
| 7,050,851 B2 | 5/2006 | Plombon et al. | | |
| 7,069,083 B2 | 6/2006 | Finch et al. | | |
| 7,096,064 B2 | 8/2006 | Deno et al. | | |
| 7,117,039 B2 | 10/2006 | Manning et al. | | |
| 7,195,637 B2 | 3/2007 | Mika | | |
| 7,218,970 B2 | 5/2007 | Ley et al. | | |
| 7,225,034 B2 | 5/2007 | Ries et al. | | |
| 7,229,450 B1 | 6/2007 | Chitre et al. | | |
| 7,272,448 B1 | 9/2007 | Morgan et al. | | |
| 7,288,096 B2 | 10/2007 | Chin | | |
| 7,316,667 B2 | 1/2008 | Lindstrom et al. | | |
| 7,322,960 B2 | 1/2008 | Yamamoto et al. | | |
| 7,369,899 B2 | 5/2008 | Malinowski et al. | | |
| 7,389,134 B1 | 6/2008 | Karicherla et al. | | |
| 7,392,085 B2 | 6/2008 | Warren et al. | | |
| 7,450,997 B1 | 11/2008 | Pianca et al. | | |
| 7,496,408 B2 | 2/2009 | Ghanem et al. | | |
| 7,499,758 B2 | 3/2009 | Cates et al. | | |
| 7,539,542 B1 | 5/2009 | Malinowski | | |
| 7,627,375 B2 | 12/2009 | Bardy et al. | | |
| 7,655,014 B2 | 2/2010 | Ko et al. | | |
| 7,684,864 B2 | 3/2010 | Olson et al. | | |
| 7,736,330 B2 | 6/2010 | Bardy | | |
| 7,761,150 B2 | 7/2010 | Ghanem et al. | | |
| 7,765,014 B2 | 7/2010 | Eversull et al. | | |
| 7,801,622 B2 | 9/2010 | Camps et al. | | |
| 7,837,671 B2 | 11/2010 | Eversull et al. | | |
| 7,846,088 B2 | 12/2010 | Ness | | |
| 7,850,610 B2 | 12/2010 | Ferek-Petric | | |
| 7,890,191 B2 | 2/2011 | Rutten et al. | | |
| 7,908,015 B2 | 3/2011 | Lazeroms et al. | | |
| 7,920,915 B2 | 4/2011 | Mann et al. | | |
| 7,930,028 B2 | 4/2011 | Lang et al. | | |
| 7,930,040 B1 | 4/2011 | Kelsch et al. | | |
| 7,983,765 B1 | 7/2011 | Doan et al. | | |
| 8,060,207 B2 | 11/2011 | Wallace et al. | | |
| 8,065,020 B2 | 11/2011 | Ley et al. | | |
| 8,066,702 B2 | 11/2011 | Rittman, III et al. | | |
| 8,090,451 B2 | 1/2012 | Tyson, Jr. | | |
| 8,155,755 B2 | 4/2012 | Flynn et al. | | |
| 8,157,813 B2 | 4/2012 | Ko et al. | | |
| 8,165,696 B2 | 4/2012 | McClure et al. | | |
| 8,260,436 B2 | 9/2012 | Gerber et al. | | |
| 8,280,527 B2 | 10/2012 | Eckerdal et al. | | |
| 8,340,779 B2 | 12/2012 | Harris et al. | | |

(56)                References Cited

U.S. PATENT DOCUMENTS

| 8,355,786  | B2   | 1/2013   | Malinowski               |
| 8,386,052  | B2   | 2/2013   | Harris et al.            |
| 8,394,079  | B2   | 3/2013   | Drake et al.             |
| 8,435,208  | B2   | 5/2013   | Bardy                    |
| 8,442,620  | B2   | 5/2013   | Silipo et al.            |
| 8,444,696  | B2   | 5/2013   | Michelson                |
| 8,452,421  | B2   | 5/2013   | Thenuwara et al.         |
| 8,478,424  | B2   | 7/2013   | Tronnes                  |
| 8,478,426  | B2   | 7/2013   | Barker                   |
| 8,489,189  | B2   | 7/2013   | Tronnes                  |
| 8,594,809  | B2   | 11/2013  | Yang et al.              |
| 8,686,052  | B2   | 4/2014   | Niitsu et al.            |
| 8,886,311  | B2   | 11/2014  | Anderson et al.          |
| 9,126,031  | B2   | 9/2015   | Tekmen et al.            |
| 9,717,923  | B2   | 8/2017   | Thompson-Nauman et al.   |
| 10,471,267 | B2   | 11/2019  | Thompson-Nauman et al.   |
| 10,525,272 | B2   | 1/2020   | Thompson-Nauman et al.   |
| 10,532,203 | B2   | 1/2020   | Thompson-Nauman et al.   |
| 10,556,117 | B2   | 2/2020   | Thompson-Nauman et al.   |
| 10,668,270 | B2   | 6/2020   | Thompson-Nauman et al.   |
| 10,668,702 | B2   | 6/2020   | Yang et al.              |
| 10,688,270 | B2   | 6/2020   | Sims et al.              |
| 11,344,737 | B2 * | 5/2022   | Thompson-Nauman .................... A61N 1/39622 |
| 2002/0049476 | A1 | 4/2002   | Bardy et al.             |
| 2002/0120294 | A1 | 8/2002   | Kroll                    |
| 2003/0088278 | A1 | 5/2003   | Bardy et al.             |
| 2003/0114908 | A1 | 6/2003   | Flach                    |
| 2004/0059348 | A1 | 3/2004   | Geske et al.             |
| 2004/0102829 | A1 | 5/2004   | Bonner et al.            |
| 2004/0143284 | A1 | 7/2004   | Chin                     |
| 2004/0210293 | A1 | 10/2004  | Bardy et al.             |
| 2004/0215240 | A1 | 10/2004  | Lovett et al.            |
| 2004/0215308 | A1 | 10/2004  | Bardy et al.             |
| 2004/0230279 | A1 | 11/2004  | Cates et al.             |
| 2004/0230280 | A1 | 11/2004  | Cates et al.             |
| 2004/0230281 | A1 | 11/2004  | Heil et al.              |
| 2004/0230282 | A1 | 11/2004  | Cates et al.             |
| 2004/0236396 | A1 | 11/2004  | Coe et al.               |
| 2005/0049663 | A1 | 3/2005   | Harris et al.            |
| 2005/0131505 | A1 | 6/2005   | Yokoyama                 |
| 2005/0277990 | A1 | 12/2005  | Ostroff et al.           |
| 2005/0288758 | A1 | 12/2005  | Jones et al.             |
| 2006/0041295 | A1 | 2/2006   | Okypka                   |
| 2006/0116746 | A1 | 6/2006   | Chin                     |
| 2006/0122676 | A1 | 6/2006   | Ko et al.                |
| 2006/0136004 | A1 | 6/2006   | Cowan et al.             |
| 2006/0161205 | A1 | 7/2006   | Mitrani et al.           |
| 2006/0247753 | A1 | 11/2006  | Wenger et al.            |
| 2006/0253181 | A1 | 11/2006  | Schulman et al.          |
| 2006/0265018 | A1 | 11/2006  | Smith et al.             |
| 2007/0023947 | A1 | 2/2007   | Ludwig et al.            |
| 2007/0049975 | A1 | 3/2007   | Cates et al.             |
| 2007/0088394 | A1 | 4/2007   | Jacobson                 |
| 2007/0100409 | A1 | 5/2007   | Worley et al.            |
| 2007/0179388 | A1 | 8/2007   | Larik et al.             |
| 2007/0208402 | A1 | 9/2007   | Helland et al.           |
| 2007/0249992 | A1 | 10/2007  | Bardy                    |
| 2008/0046056 | A1 | 2/2008   | O'Connor                 |
| 2008/0243219 | A1 | 10/2008  | Malinowski et al.        |
| 2008/0269716 | A1 | 10/2008  | Bonde et al.             |
| 2009/0157091 | A1 | 6/2009   | Buysman                  |
| 2009/0222021 | A1 | 9/2009   | Chang                    |
| 2009/0259283 | A1 | 10/2009  | Brandt et al.            |
| 2009/0264780 | A1 | 10/2009  | Schilling                |
| 2009/0270962 | A1 | 10/2009  | Yang et al.              |
| 2010/0016935 | A1 | 1/2010   | Strandberg et al.        |
| 2010/0030227 | A1 | 2/2010   | Kast et al.              |
| 2010/0030228 | A1 | 2/2010   | Havel                    |
| 2010/0042108 | A1 | 2/2010   | Hibino                   |
| 2010/0056858 | A1 | 3/2010   | Mokelke et al.           |
| 2010/0094252 | A1 | 4/2010   | Wengreen et al.          |
| 2010/0113963 | A1 | 5/2010   | Smits et al.             |
| 2010/0125194 | A1 | 5/2010   | Bonner et al.            |
| 2010/0137879 | A1 | 6/2010   | Ko et al.                |

| 2010/0152747 | A1 | 6/2010   | Padiy et al.             |
| 2010/0152798 | A1 | 6/2010   | Sanghera et al.          |
| 2010/0211064 | A1 | 8/2010   | Mahapatra et al.         |
| 2010/0217298 | A1 | 8/2010   | Bardy                    |
| 2010/0217301 | A1 | 8/2010   | Bardy                    |
| 2010/0241185 | A1 | 9/2010   | Mahapatra et al.         |
| 2010/0249696 | A1 | 9/2010   | Bardy                    |
| 2010/0305428 | A1 | 12/2010  | Bonner et al.            |
| 2010/0318098 | A1 | 12/2010  | Lund et al.              |
| 2011/0009933 | A1 | 1/2011   | Barker                   |
| 2011/0077708 | A1 | 3/2011   | Ostroff                  |
| 2011/0125163 | A1 | 5/2011   | Rutten et al.            |
| 2011/0224680 | A1 | 9/2011   | Barker                   |
| 2011/0224681 | A1 | 9/2011   | McDonald                 |
| 2011/0257660 | A1 | 10/2011  | Jones et al.             |
| 2012/0016377 | A1 | 1/2012   | Geroy                    |
| 2012/0029335 | A1 | 2/2012   | Sudam et al.             |
| 2012/0078266 | A1 | 3/2012   | Tyson, Jr.               |
| 2012/0089153 | A1 | 4/2012   | Christopherson et al.    |
| 2012/0097174 | A1 | 4/2012   | Spotnitz et al.          |
| 2012/0123496 | A1 | 5/2012   | Schotzko et al.          |
| 2012/0191106 | A1 | 7/2012   | Ko et al.                |
| 2012/0209283 | A1 | 8/2012   | Zhu                      |
| 2012/0209285 | A1 | 8/2012   | Barker et al.            |
| 2012/0209286 | A1 | 8/2012   | Papay et al.             |
| 2012/0220849 | A1 | 8/2012   | Brockway et al.          |
| 2012/0316613 | A1 | 12/2012  | Keefe et al.             |
| 2013/0041345 | A1 | 2/2013   | Kilcoin et al.           |
| 2013/0103049 | A1 | 4/2013   | Bonde                    |
| 2013/0158564 | A1 | 6/2013   | Harris et al.            |
| 2013/0238067 | A1 | 9/2013   | Baud ina                 |
| 2014/0330325 | A1 | 11/2014  | Thompson-Nauman et al.   |
| 2014/0330326 | A1 | 11/2014  | Thompson-Nauman et al.   |
| 2014/0330329 | A1 | 11/2014  | Thompson-Nauman et al.   |
| 2014/0330331 | A1 | 11/2014  | Thompson-Nauman et al.   |
| 2020/0069952 | A1 | 3/2020   | Thompson-Nauman et al.   |
| 2020/0129755 | A1 | 4/2020   | Thompson-Nauman et al.   |
| 2020/0147402 | A1 | 5/2020   | Thompson-Nauman et al.   |
| 2020/0289816 | A1 | 9/2020   | Thompson-Nauman et al.   |
| 2022/0249855 | A1 | 8/2022   | Thompson-Nauman et al.   |

FOREIGN PATENT DOCUMENTS

| EP | 0347353    | A1 | 12/1989 |
| EP | 1541191    | A1 | 6/2005  |
| FR | 2773491    | A1 | 7/1999  |
| JP | 2007500549 | A  | 1/2007  |
| WO | 9938568    | A1 | 8/1999  |
| WO | 2001023035 | A1 | 4/2001  |
| WO | 02242275   | A2 | 3/2002  |
| WO | 0226315    | A1 | 4/2002  |
| WO | 0241946    | A2 | 5/2002  |
| WO | 2004073506 | A2 | 9/2004  |
| WO | 2005011809 | A2 | 2/2005  |
| WO | 2006060705 | A1 | 6/2006  |
| WO | 20100047893 | A1 | 4/2010 |

OTHER PUBLICATIONS

"Pharmacological and Electrical Cardioversion of AF," Europace Supplements, vol. 2, Jan. 2001, 1 pp.

"SQ-RX Pulse Generator, a Component of the S-ICD System, User's Manual, Model 1010," Cameron Health, Inc., Dec. 2, 2008, 46 pp.

"St. Jude Medical Announces Filing of PMA Supplement for Ventritex Angstrom MD and Contour MD ICD's," St. Jude Medical, Inc., Jun. 5, 1998, 1 pp.

Alexander et al., "Implications of Implantable Cardioverter Defibrillator Therapy in Congenital Heart Disease and Pediatrics," Journal of Cardiovascular Electrophysiology, vol. 15, No. 1, Jan. 2004, 5 pages.

Avogadros Lab Supply Inc., Catalog; Scoopula with Beech Wood Handle, can be found on-line at http://www. avogadro-lab-supply. com/search.php, accessed Oct. 6, 2013, 1 page.

Baddour et al., Update on Cardiovascular Implantable Electronic Device Infections and their Management—A Scientific Statement

(56)        References Cited

OTHER PUBLICATIONS from the American Heart Association, Circulation available at http://circ.ahajournals.org, Jan. 26, 2010, 23 pages.

Bardy et al., "A Simplified, Single-Lead Unipolar Transvenous Cardioversion-Defibrillation System," Circulation, vol. 8, No. 2, Aug. 1993, 5 pp.

Bardy et al., "An Entirely Subcutaneous Implantable Cardioverter-Defibrillator," The New England Journal of Medicine, May 2010, 9 pp.

Baudoin et al., "The Superior Epigastric Artery Does Not Pass Through Larrey's Space (Trigonurn Sternocostale)" Surgical Radial Anal (2003), 25, Aug. 2003, pp. 259-262.

Bauersfeld et al., "Initial Experience with Implantable Cardioverter Defibrillator Systems Using Epicardial and Pleural Electrodes in Pediatric Patients," The Annals of Theoracic Surgery, 2007, vol. 84, 3 pages.

Berul et al., "Minmally Invasive Cardioverter Defibrillator Implantation for Children: An Animal Model and Pediatric Case Report," Journal of Pacing and Clinical Electrophysiology, Dec. 2001, vol. 24, No. 12, 6 pages.

Bielefeld et al., "Thoracoscopic Placement of Implantable Cardioverter-Defibrillator Patch Leads in Sheep", Circulation; Nov. 1993, vol. 88, No. 5, Part 2; 5 pages.

Bocker et al., "Treatment with implantable defibrillators in childhood," Herzschr Elektrophys, accepted Nov. 11, 1999, 4 pp.

Bolling et al., "Automatic Internal Cardioverter Defibrillator: A Bridge to Heart Transplantation", Heart Lung Transplantation, Abstract Only, Jul.-Aug. 1991, 1 page.

Boston Scientific, "Dr. Lucas Boersma Shares Insight into the S-ICD Effortless 3-year Analysis," retrieved from http://www.bostonscientific.com/en-EU/products/defibrillators/s-icd-emblem/clinical-data.html on Nov. 24, 2016, 3 pp.

Cigna et al., "A New Technique for Substernal Colon Transposition with A Breast Dissector: Report of 39 Cases", Journal of Plastic, Reconstructive and Aesthetic Surgery, 2006:59, 4 pages.

Copper, et al., "Implantable Cardioverter Defibrillator Lead Complications and Laser Extraction in Children and Young Adults with Congenital Heart Disease: Implications for Implantation and Management," Journal of Cardiovascular Electrophysiology, vol. 14, No. 4, Apr. 2003, 7 pages.

Damiano, "Implantation of Cardioverter Defibrillators in the Post-Sternotomy Patient", The Annals of Thoracic Surgery, 1992; 53: pp. 978-983.

Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.

Erickson, MD., "Non-thoracotomy ICD Implantation in Pediatric and Adult Congenital Heart Disease Patients," Oct. 2015, 44 slides.

Falk et al., "External Cardiac Pacing Using Low Impedance Electrodes Suitable for Defibrillation: A Comparative Blinded Study," Journal of American College of Cardiology, vol. 22, No. 5, Nov. 1, 1993, 5 pages.

Fischbach et al., "Use a Single Coil Transvenous Electrode with an Abdominally Placed Implantable Cardioverter Defibrillator in Children," Place, vol. 23, May 2000, 5 pp.

Frame et al., "Long-Term Stability of Defibrillation Thresholds with Intrapericardial Defibrillator Patches", Pacing and Clinical Electrophysiology, Jan. 1993, Part II, vol. 16, 6 pages.

Ganapathy et al., ""Implantable Device to Monitor Cardiac Activity with Sternal Wires,"" Pace, vol. 37, Dec. 2014, 11 pages.

Gradaus et al., "Nonthoracotomy Implantable Cardioverter Defibrillator Placement in Children: Use of Subcutaneous Array Leads and Abdominally Placed Implantable Cardioverter Defibrillators in Children," Journal of Cardiovascular Electrophysiology, vol. 12, No. 3, Mar. 2001, 5 pp.

Guenther et al., ""Substernal Lead Implantation: A Novel Option to Manage OFT Failure in S-ICD patients,"" Clinical Research Cardiology, Published On-line Oct. 2, 2014, 3 pages.

Haffajee et al., "A Multicenter, Randomized Trial Comparing an Active Can Implantable Defibrillator with a Passive Can System" Pace, vol. 20, Jan. 1997, Part II, 5 pp.

Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.

Haydin et al., "Subxiphoid Approach to Epicardial Implantation of Implantable Cardioverter Defibrillators in Children", Pace, vol. 36, Aug. 2013, 5 pages.

Hoffmann et al., "experience with pectoral versus abdominal implantation of a small defibrillator," European Heart Journal, vol. 19, Jul. 1998, 14 pp.

Hsia et al., "Novel Minimally Invasive, Intrapericardial Implantable Cardioverter Defibrillator Coil System: A Useful Approach to Arrhythmia Therapy in Children," The Annals of Thoracic Surgery, 2009, vol. 87; 6 pages.

Juchem et al., "Successful use of transvenous coil electrodes as single element subcutaneous array leads," published online Jan. 14, 2009, 4 pp.

Karwande et al., "Bilateral Anterior Thoracotomy for Automatic Implantable Cardioverter Defibrillator Placement in Patients with Previous Sternotomy", The Annals of Thoracic Surgery; Oct. 1992; 54(4); 3 pages.

Kriebel et al., "Implantation of an 'extracardiac' internal cardioverter defibrillator in a 6-month-old infant," Zeitschrift fur Kardiologie, Jan. 18, 2005, 4 pp.

Kuschyk et al., "A Multcenter Study of Shock Pathways for Subcutaneous Implantable Defibrillators," Journal of Cardiovascular Electrophysiology, vol. 25, No. 1, Jan. 2014, 7 pp.

Laudon, M. K., "Pulse Output", Chapter 11 of Design of Pacemakers, Published by the Institute of Electrical and Electronics Engineers, Inc., New York, (1995), 30 pages.

Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.

Lemmer, "Defibrillator Patch Constriction, Letter to the Editor", The Annals of Thoracic Surgery, 1996, 1 page.

Medtronic, Inc. 6996SQ Subcutaneous, Unipolar Lead with Defibrillation Coil Electrode, Technicial Manual, (Applicant points out, in accordance with MPEP 609.04(a), that the year of publication, 2012, is sufficiently earlier than the effective U.S. filing date, so that the particular month of publication is not in issue.), 2012, 22 pages.

Medtronic, Inc. 6996T Tunneling Tool, Technical Manual, (Applicant points out, in accordance with MPEP 609.04(a), that the year of publication, 2011, is sufficiently earlier than the effective U.S. filing date, so that the particular month of publication is not in issue.), 2011 12 pages.

Mitchell et al., "Experience with an Implantable Tiered Therapy Device Incorporating Antitachycardia Pacing and Cardioverter/ Defibrillator Therapy", Thoracic and Cardiovascular Surgery, Abstract Only, Mar. 1993, 1 page.

Molina et al, "An Epicardial Subxiphoid Implantable Defibrillator Lead: Superior Effectiveness After Failure of Sindard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.

Obadia et al., "Thoracoscopic Approach to Implantable Cardioverter Defibrillator Patch Electrode Implantation", Pacing and Clinical Electrophysiology; Jun. 1996; vol. 19; 6 pages.

Obadia, et al., "New Approach for Implantation of Automatic Defibrillators Using Videothoracoscopy", Journal Ann Cardiel Angeiol (Paris); Sep. 1994; 43 (7) Abstract Only, 1 page.

Olson et al., "Onset and Stability for Ventricular Tachyarrhythmia Detection in an Implantable Pacer-Cardioverter-Defibrillator," IEEE, 1987, 4 pp. (Applicant points out, in accordance with MPEP 609.04(a), that the year of publication, 1987, is sufficiently earlier than the effective U.S. filing date, so that the particular month of publication is not in issue.).

Park et al., "Use of an Implantable Cardioverter Defibrillator in an Eight-Moth-Old Infant with Ventricular Fibrillation Arising from a Myocardial Fibroma," Pace, vol. 22, Jan. 1999, Part I, 2 pp.

(56) References Cited

OTHER PUBLICATIONS

Pebax Product Brochure, 14 pages and can be found on-line at http://www.pebax.com/export/sites/pebaxl.contentlmedias/downloads/literature/pebax-product-range-brochure.pdf. accessed on-line at the above address on Jul. 27, 2017, 14 pages.

Piccione, et al., "Erosion of Extrapericardial Implantable Cardioverter Defibrillator Patch Through the Gastic Fundus with Fistulous Tract Information", Cardiology in Review; 2006; 14, e21-e23 pages.

Prosecution History from U.S. Appl. No. 14/261,456, now U.S. Pat. No. 10,556,117, dated May 25, 2016 through Dec. 12, 2019, 190 pp.

Prosecution History from U.S. Appl. No. 14/261,460, now U.S. Pat. No. 9,717,923, dated May 13, 2016 through May 11, 2017, 29 pp.

Prosecution History from U.S. Appl. No. 14/261,470, now U.S. Pat. No. 10,471,267, dated Jun. 5, 2017 through Oct. 3, 2019, 199 pp.

Prosecution History from U.S. Appl. No. 14/261,479, now U.S. Pat. No. 10,532,203, dated May 25, 2016 through Dec. 12, 2019, 176 pp.

Prosecution History from U.S. Appl. No. 14/261,488, now U.S. Pat. No. 10,668,270, dated May 25, 2016 through Apr. 30, 2020, 288 pp.

Prosecution History from U.S. Appl. No. 15/661,365, now U.S. Pat. No. 10,525,272, dated Oct. 12, 2017 through Dec. 9, 2019, 106 pp.

Prosecution History from U.S. Appl. No. 16/678,365, now U.S. Pat. No. 11,344,737, dated Jan. 10, 2020 through May 3, 2022, 35 pp.

Prosecution History from U.S. Appl. No. 16/725,458, now U.S. Pat. No. 11,344,720, dated Mar. 25, 2020 through May 4, 2022, 38 pp.

Prosecution History from U.S. Appl. No. 16/742,385, dated Oct. 6, 2021 through Sep. 2, 2022, 54 pp.

Prosecution History from U.S. Appl. No. 16/885,837, dated Jun. 17, 2020 through May 13, 2022, 32 pp.

Prosecution History of Opposition from European Patent No. 1318856, dated Apr. 15, 2015 through Apr. 10, 2017, 312 pp.

Quigley et al., "Migration of an Automatic Implantable Cardioverter-Defibrillator Patch Causing Massive Hemothorax", Journal Texas Heart Institute, Nov. 1, 1996; vol. 23, 4 pages.

Schuder et al., "Experimental Ventricular Defibrillation with an Automatic and Completely Implanted System," Trans. Amer. Soc. Artif. Int. Organs, vol. XVI, 1970, (Applicant points out, in accordance with MPEP 609.04(a), that the year of publication, 1970, is sufficiently earlier than the effective U.S. filing date, so that the particular month of publication is not in issue.).

Schuder et al., "Ventricular Defibrillation in the Dog Using Implanted and Partially Implanted Electrode Systems," The American Journal of Cardiology, vol. 33, Feb. 1974, 5 pp.

Schuder, "The Role of an Engineering Oriented Medical Research Group in Developing Improved Methods ad Devices for Achieving Ventricular Defibrillation the University of Missouri Experience," Pace, vol. 16, Jan. 1993, 30 pp.

Sgoifo et al., "Electrode Positioning for Reliable Telemetry ECG Recordings During Social Stress in Unrestrained Rats," Physiology and Behaviors, vol. 60, issue 6, Dec. 1996, pp. 1397-1401.

Shapira, et al., "A Simplied Method for Implantation of Automatic Cardioverter Defibrillator in Patients with Previous Cardiac Surgery", Pacing and Clinical Electrophysiology, January Part I, 1993, vol. 16; 6 pages.

Steinke et al., "Subepicardial Infarction, Myocardial Impression, and Ventricular Penetration by Sutureless Electrode and Leads", Chest; 70: 1, Jul. 1976, 2 pages.

Thogersen et al., "Implantable Cardioverter Defibrillator in a 4-Month-Old Infant with Cardiac Arrest Associated with a Vascular Heart Tumor," accepted Jan. 8, 2001, Pace, vol. 24, Nov. 2001, 2 pp.

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.ulsus.com/ccc2007/abs/0697.htm, 2 pages.

Tung et al., "Minimal Invasive Extra Cardiac Placement of High Voltage Defibrillator Leads", Poster 3; S200 Abstract, P0-3-4; St. Paul Hospital, Vancouver, British Columbia, Canada, 1 pages.

Tung et al., Invention Disclosure Form for "Hybrid Endovascular and Extrvascular Implantable Cardioverter-Defibrillator System", Mar. 2006, 10 pages.

U.S. Appl. No. 17/930,994, filed Sep. 9, 2022, naming inventors Thompson-Nauman et al.

Vyhmeister et al., "Simple Approach for Extrapericardial Placement of Defibrillator Patches via Median Sternotomy", The Annals of Thoracic Surgery; 1994; 57:4 pages.

Weiss et al., Safety and Efficacy of a Totally Subcutaneous Implantable-Cardioverter Defibrillator, Arrhythmia/Electrophysiology, Jun. 28, 2013, 11 pp.

Response to Office Action dated Sep. 2, 2022 from U.S. Appl. No. 16/742,385, filed Nov. 29, 2022, 10 pp.

Notice of Allowance from U.S. Appl. No. 16/742,385 dated Aug. 8, 2023, 5 pp.

Response to Office Action dated Mar. 16, 2023 from U.S. Appl. No. 16/742,385, filed Jul. 17, 2023, 11 pp.

Final Office Action from U.S. Appl. No. 16/742,385 dated Mar. 16, 2023, 9 pp.

Response to Office Action dated May 24, 2024 from U.S. Appl. No. 17/930,994, filed Aug. 26, 2024, 14 pp.

Response to Office Action dated May 31, 2024 from U.S. Appl. No. 17/661,103, filed Aug. 29, 2024, 11 pp.

Office Action from U.S. Appl. No. 17/661,103 dated May 31, 2024, 11 pp.

Office Action from U.S. Appl. No. 17/930,994 dated May 24, 2024, 7 pp.

Final Office Action from U.S. Appl. No. 17/661,103 dated Dec. 4, 2024, 10 pp.

Final Office Action from U.S. Appl. No. 17/930,994 dated Dec. 20, 2024, 9 pp.

Response to Final Office Action dated Dec. 4, 2024 from U.S. Appl. No. 17/661,103, filed Jan. 27, 2025, 14 pp.

Response to Final Office Action dated Dec. 20, 2024 from U.S. Appl. No. 17/930,994, filed Feb. 20, 2025, 12 pp.

Final Office Action from U.S. Appl. No. 17/661,103 dated Mar. 3, 2025, 10 pp.

Advisory Action from U.S. Appl. No. 17/661,103 dated Jun. 3, 2025, 3 pp.

Response to Final Office Action dated Mar. 3, 2025 from U.S. Appl. No. 17/661,103, filed May 2, 2025, 15 pp.

Corrected Notice of Allowance from U.S. Appl. No. 17/661,103 dated Aug. 4, 2025, 2 pp.

Notice of Allowance from U.S. Appl. No. 17/661,103 dated Jul. 23, 2025, 5 pp.

Response to Final Office Action dated Mar. 3, 2025 from U.S. Appl. No. 17/661,103, filed Jul. 3, 2025, 12 pp.

Advisory Action from U.S. Appl. No. 17/930,994 dated Mar. 28, 2025, 8 pp.

* cited by examiner

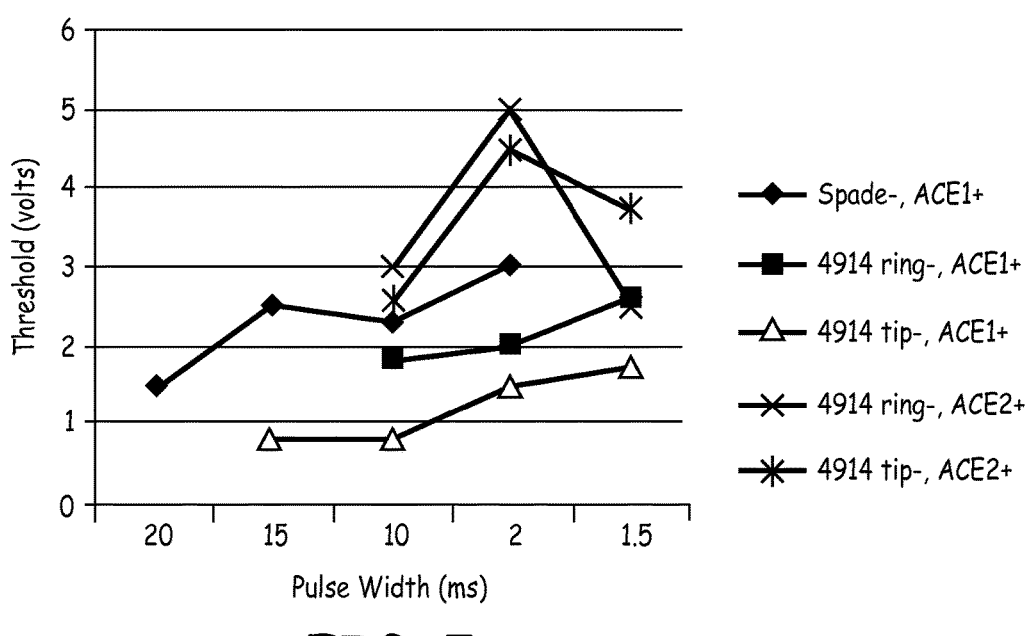
FIG. 5
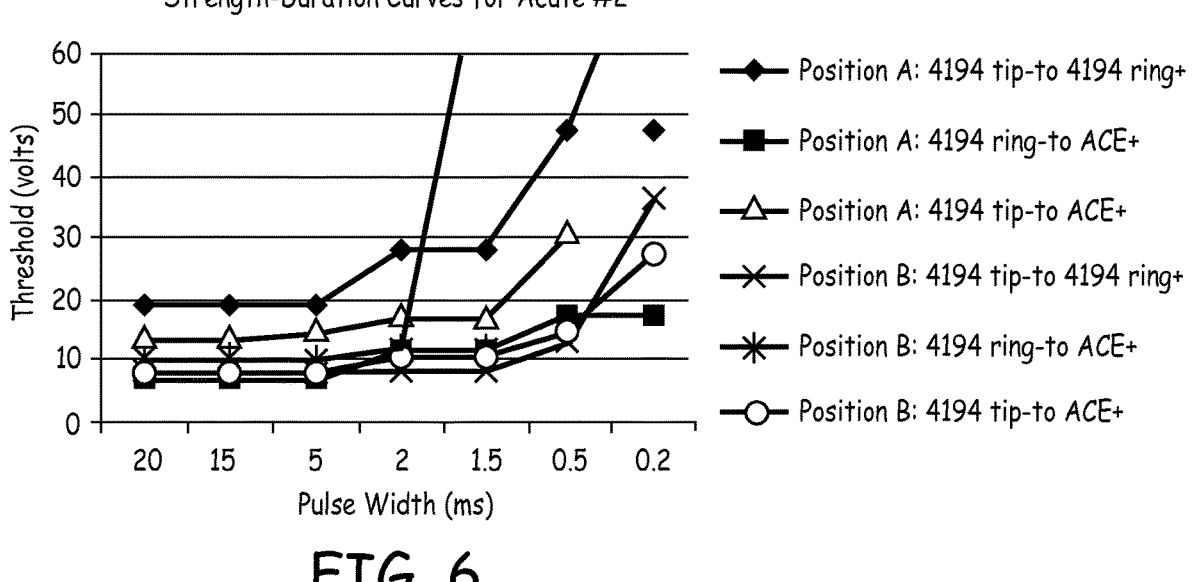
FIG. 6

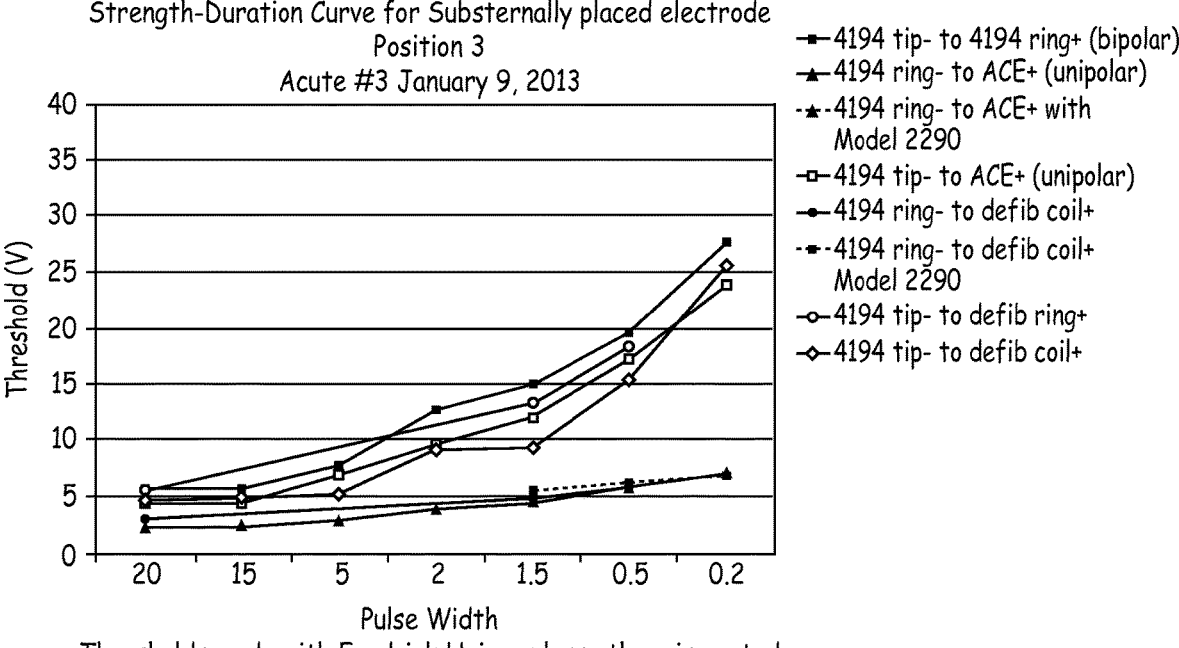

Strength-Duration Curve for Substernally placed electrode
Position 3
Acute #3 January 9, 2013

-■-4194 tip- to 4194 ring+ (bipolar)
-▲-4194 ring- to ACE+ (unipolar)
--▲-4194 ring- to ACE+ with
   Model 2290
-□-4194 tip- to ACE+ (unipolar)
-●-4194 ring- to defib coil+
--■-4194 ring- to defib coil+
   Model 2290
-○-4194 tip- to defib ring+
-◇-4194 tip- to defib coil+

Threshold (V)

Pulse Width

Thresholds made with Fredrick Heier unless otherwise noted

FIG. 7

Strength-Duration Curve for Substernally placed electrode
Position 4
Acute #3 January 9, 2013

-▲- 4194 tip- to 4194 ring+ (bipolar)
-✕- 4194 ring- to ACE+ (unipolar)
-◆- 4194 ring- to ACE+ (unipolar) with
   Model 2290
-■- 4194 tip- to ACE+ (unipolar)
-●- 4194 tip- to defib coil+

Threshold (V)

Pulse Width

Thresholds made with Fredrick Heier unless otherwise noted

FIG. 8

SUBSTERNAL ELECTRICAL STIMULATION SYSTEM

This application is a continuation of U.S. application Ser. No. 16/725,458, filed Dec. 23, 2019 (issued as U.S. Pat. No. 11,344,720), which is a divisional of U.S. application Ser. No. 14/261,479, filed Apr. 25, 2014 (issued as U.S. Pat. No. 10,532,203), which claims the benefit of U.S. Provisional Application No. 61/820,033, filed on May 6, 2013. The content of each of these applications is incorporated herein by reference in its entirety.

FIELD OF THE INVENTION

The present application relates to electrical stimulation devices, systems and/or methods for providing substernal electrical stimulation, including substernal cardiac pacing.

BACKGROUND OF THE INVENTION

Implantable pulse generators have been utilized to provide electrical stimulation to various organs, tissues, muscle, nerves or other features of a patient's body. One example of electrical stimulation provided to a patient is cardiac pacing. Cardiac pacing electrically stimulates the heart when the heart's natural pacemaker and/or conduction system fails to provide synchronized atrial and ventricular contractions at appropriate rates and intervals for a patient's needs. When a patient's heart is beating too slow, bradycardia pacing increases the rate at which the patient's heart contracts to provide relief from symptoms associated with bradycardia. Cardiac pacing may also provide electrical overdrive stimulation intended to suppress or convert tachyarrhythmias, again supplying relief from symptoms and preventing or terminating arrhythmias that could lead to sudden cardiac death or need to be treated with high voltage defibrillation or cardioversion shocks.

Pacemakers typically require at least two electrodes to deliver electrical stimulation therapy to the heart and to sense electrical activity of the heart. Traditionally, pacemaker systems are comprised of an implantable pulse generator (or pacemaker) coupled to one or more leads. The lead(s) include one or more electrodes on a distal portion of the lead that are implanted inside the heart such that at least one electrode touches the endocardium. In other examples, the one or more leads can be implanted on the epicardial surface of the heart.

SUMMARY OF THE INVENTION

The present application is directed to implantable cardiac pacing systems and methods for providing substernal pacing. In one embodiment, a cardiac pacing system includes a pacemaker implanted in a patient and an implantable medical electrical lead. The implantable medical electrical lead includes an elongated lead body having a proximal end and a distal portion, a connector configured to couple to the pacemaker at the proximal end of the elongated lead body, and one or more electrodes along the distal portion of the elongated lead body, wherein the distal portion of the elongated lead body of the lead is implanted substantially within an anterior mediastinum of the patient and the pacemaker is configured to deliver pacing pulses to a heart of the patient.

In another embodiment, a method comprises generating one or more stimulation pulses with an implantable pulse generator and delivering the one or more stimulation pulses via at least one electrode of an implantable medical electrical lead implanted at least partially within the anterior mediastinum.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF THE DRAWINGS

FIG. 5 is a graph illustrating strength-duration curves showing the capture thresholds obtained at various pulse widths during a first acute study.

FIG. 6 is a graph illustrating strength-duration curves showing the capture thresholds obtained at various pulse widths during a second acute study.

FIG. 7 is a graph illustrating strength-duration curves of electrical data from a third acute experiment.

FIG. 8 is a graph illustrating strength-duration curves of electrical data from the third acute experiment.

DETAILED DESCRIPTION

Figure 1A:
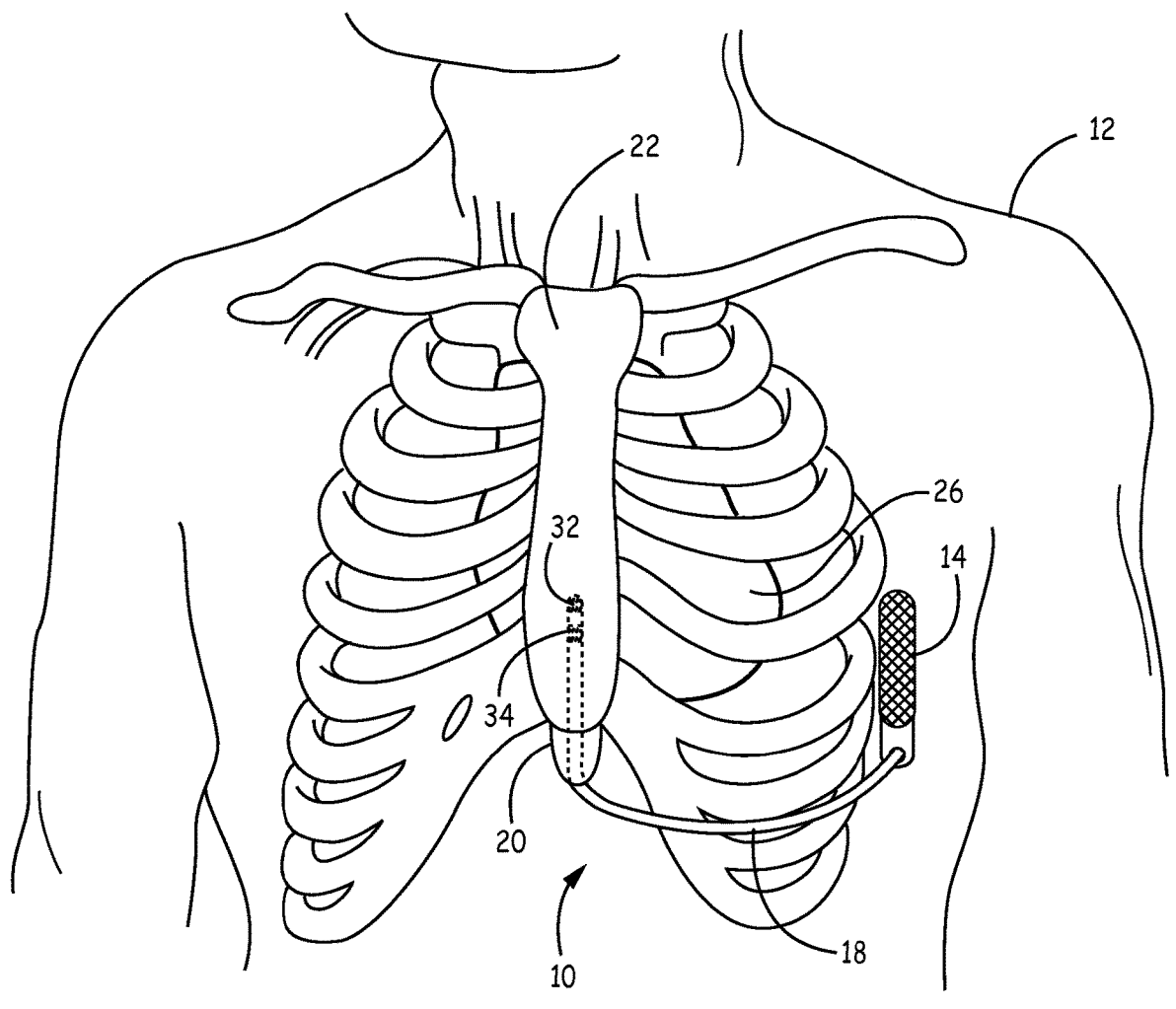
FIG. 1A is a front view of patient 12 implanted with implantable medical system 10.
Figure 1B:
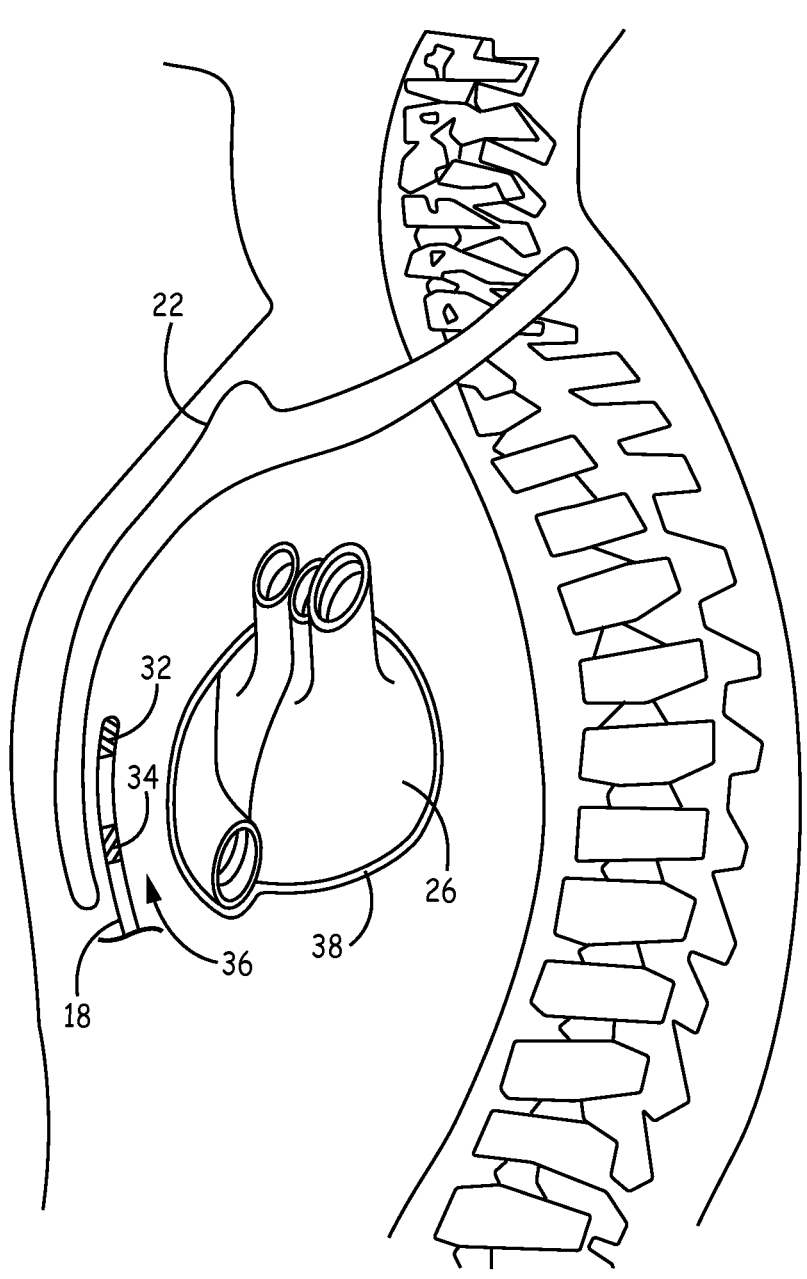
FIG. 1B is a side view of patient 12 with implantable medical system 10.
Figure 1C:
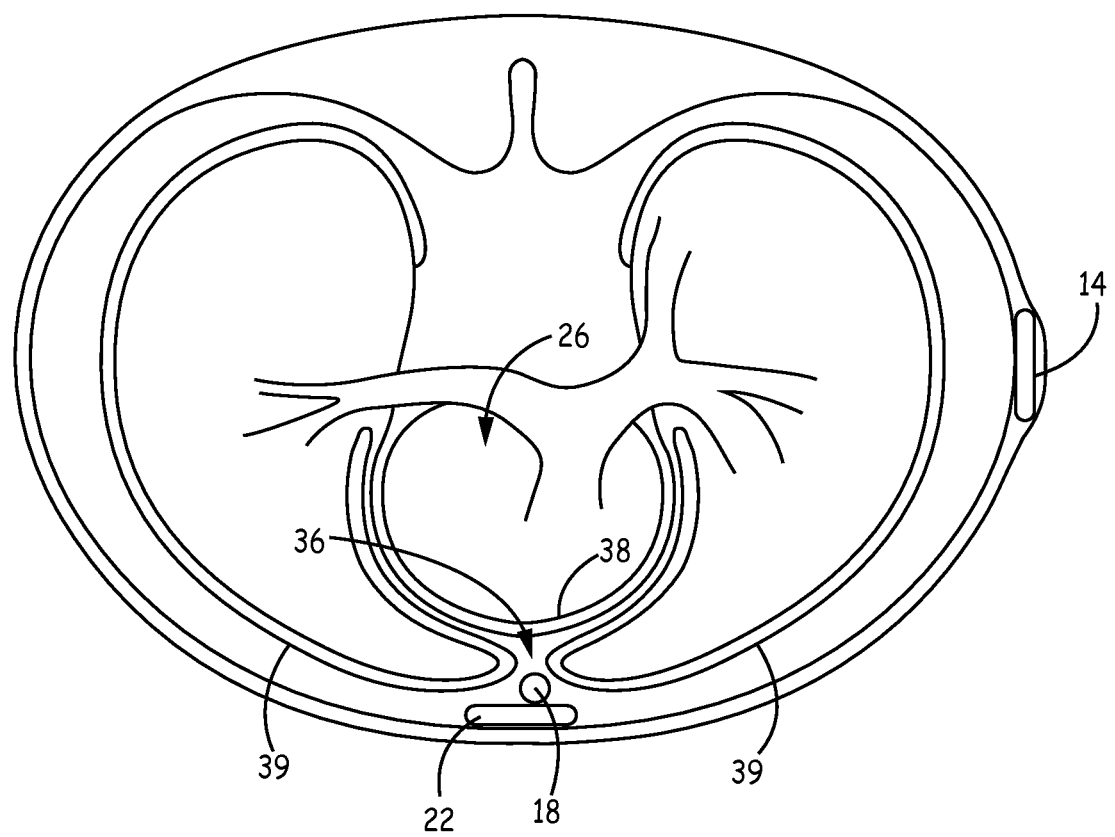
FIG. 1C is a transverse view of patient 12 with implantable medical system 10.

FIGS. 1A-C are conceptual diagrams of a patient 12 implanted with an example implantable medical system 10. FIG. 1A is a front view of patient 12 implanted with implantable medical system 10. FIG. 1B is a side view of patient 12 with implantable medical system 10. FIG. 1C is a transverse view of patient 12 with implantable medical system 10. Implantable medical system 10 includes an implantable pulse generator 14 connected to an implantable medical electrical lead 18 (referred to hereinafter as "lead 18"). FIGS. 1A-C illustrates an implantable cardiac pacing system and will be described in the context of the implantable cardiac pacing system.

Implantable pulse generator 14 is implanted subcutaneously on the left side of patient 12 above the ribcage. Implantable pulse generator 14 may, in some instances, be implanted between the left posterior axillary line and the left anterior axillary line of patient 12. Implantable pulse generator 14 may, however, be implanted at other subcutaneous locations on patient 12 as described later.

Lead 18 includes a proximal end that includes a connector configured to be connected to implantable pulse generator 14 and a distal portion that includes electrodes 32 and 34. Lead 18 extends subcutaneously above the ribcage from implantable pulse generator 14 toward a center of the torso of patient 12, e.g., toward xiphoid process 20 of patient 12. At a location near xiphoid process 20 lead 18 bends or turns and extends superior underneath/below the sternum 22 in anterior mediastinum 36. Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 18 extends along the posterior side of sternum 22 substantially within anterior mediastinum 36. For example, the distal portion of lead 18 may be substantially within the loose connective tissue of anterior mediastinum 36, which may thus hold lead 18 in place. A lead implanted with the distal portion substantially within anterior mediastinum 36 will be referred to herein as a substernal lead. Also, electrical stimulation, such as pacing, provided by a lead implanted with the distal portion substantially within anterior mediastinum 36 will be referred to herein as substernal electrical stimulation or substernal pacing.

Although the distal portion of lead 18 is described herein as being implanted substantially within anterior mediastinum 36, the distal portion of lead 18 may be implanted in other non-vascular, extra-pericardial locations, including the gap, tissue, or other anatomical features around the perimeter of and adjacent to, but not attached to, the pericardium or other portion of heart 26 and not above sternum 22 or ribcage. As such, lead 18 may be implanted anywhere within the "substernal space" defined by the undersurface between the sternum and/or ribcage and the body cavity but not including the pericardium or other portion of heart 26. The substernal space may alternatively be referred to by the terms "retrosternal space" or "mediastinum" or "infrasternal" as is known to those skilled in the art and includes the anterior mediastinum 36. The substernal space may also include the anatomical region described in Baudoin, Y. P., et al., entitled "The superior epigastric artery does not pass through Larrey's space (trigonum sternocostale)." Surg.Radiol.Anat. 25.3-4 (2003): 259-62 as Laney's space. In other words, the distal portion of lead 18 may be implanted in the region around the outer surface of heart 26, but not attached to heart 26.

The distal portion of lead 18 may be implanted substantially within anterior mediastinum 36 such that the electrodes 32 and 34 are located near a ventricle of heart 26. For instance, lead 18 may be implanted such that electrodes 32 and 34 are located over a cardiac silhouette of one or both ventricles as observed via an anterior-posterior (AP) fluoroscopic view of heart 26. In one example, lead 18 may be implanted such that a unipolar therapy vector from electrode 32 to a housing electrode of implantable pulse generator 14 and/or a unipolar therapy vector from electrode 34 to the housing electrode of implantable pulse generator 14 are substantially across the ventricles of heart 26. The therapy vector may be viewed as a line that extends from a point on electrode 32 or 34, e.g., center of electrode 32 or 34, to a point on the housing electrode of implantable pulse generator 14, e.g., center of the housing electrode. In another example, the spacing between electrodes 32 and 34 as well as the placement of lead 18 may be such that a bipolar therapy vector between electrode 32 and electrode 34 is centered or otherwise located over the ventricle. However, lead 18 may be positioned at other locations as long as one or both of the unipolar or bipolar therapy vectors using electrodes 32 and 34 result in capture of the ventricle of the heart.

In the example illustrated in FIGS. 1A-C, lead 18 is located substantially centered under sternum 22. In other instances, however, lead 18 may be implanted such that it is offset laterally from the center of sternum 22. In some instances, lead 18 may extend laterally enough such that all or a portion of lead 18 is underneath/below the ribcage in addition to or instead of sternum 22.

Lead 18 includes an elongated lead body that contains one or more elongated electrical conductors (not illustrated) that extend within the lead body from the connector at the proximal lead end to electrodes 32 and 34 located along the distal portion of lead 18. The elongated lead body may have a generally uniform shape along the length of the lead body. In one example, the elongated lead body may have a generally tubular or cylindrical shape along the length of the lead body. The elongated lead body may have a diameter of between 3 and 9 French (Fr) in some instances. However, lead bodies of less than 3 Fr and more than 9 Fr may also be utilized. In another example, the distal portion (or all of) the elongated lead body may have a flat, ribbon or paddle shape. In this instance, the width across the flat portion of the flat, ribbon or paddle shape may be between 1 and 3.5 mm. Other lead body designs may be used without departing from the scope of this disclosure. The lead body of lead 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead body of lead 18 may engage with respective ones of electrodes 32 and 34. In one example, each of electrodes 32 and 34 is electrically coupled to a respective conductor within the lead body. The respective conductors may electrically couple to circuitry, such as a therapy module or a sensing module, of implantable pulse generator 14 via connections in connector assembly, including associated feedthroughs. The electrical conductors transmit therapy from a therapy module within implantable pulse generator 14 to one or more of electrodes 32 and 34 and transmit sensed electrical signals from one or more of electrodes 32 and 34 to the sensing module within implantable pulse generator 14.

Electrodes 32 and 34 may comprise ring electrodes, hemispherical electrodes, coil electrodes, helix electrodes, segmented electrodes, directional electrodes, ribbon electrodes, or other types of electrodes, or combination thereof. Electrodes 32 and 34 may be the same type of electrodes or different types of electrodes. In the example illustrated in FIGS. 1A-C electrode 32 is a hemispherical electrode and electrode 34 is a ring or coil electrode. Electrodes 32 and 34 of lead 18 may have substantially the same outer diameter as the lead body. In one example, electrodes 32 and 34 may have surface areas between 1.6-55 mm$^2$. In another example, one or both of electrodes 32 and 34 may be coil electrodes and may have surface areas of up to 200 mm$^2$. Electrodes 32 and 34 may, in some instances, have relatively the same surface area or different surface areas. For example, electrode 32 may have a surface area of approximately 2-5 mm² and electrode 34 may have a surface area between 15-44 mm².

In some instances, electrodes 32 and 34 may be spaced apart by approximately 5-15 mm. In other instances, electrodes 32 and 34 may be spaced apart by distances greater than 15 mm. For example, electrodes 32 and 34 may be spaced apart between 2-8 cm and still both be substantially over the ventricles. In another example, electrodes 32 and 34 may be spaced apart by greater than 8 cm, e.g., up to 16 cm apart, as may be the case to obtain atrial and ventricular pacing.

The example dimensions provided above are exemplary in nature and should not be considered limiting of the embodiments described herein. In other examples, lead 18 may include a single electrode or more than two electrodes. In further examples, lead 18 may include one or more additional electrodes outside of the substernal space, e.g., near the apex of the heart or near a proximal end of lead 18.

Implantable pulse generator 14 may generate and deliver electrical stimulation pulses, such as pacing pulses, to heart 26 via a therapy vector that includes any unipolar or bipolar therapy vector formed via combinations of electrodes 32 and 34 and the housing electrode of implantable pulse generator 14. For example, implantable pulse generator 14 may deliver pacing pulses using a bipolar therapy vector between electrodes 32 and 34. In another example, implantable pulse generator 14 may deliver pacing pulses using a unipolar therapy vector (e.g., between electrode 32 and the conductive housing electrode of implantable pulse generator 14 or between electrode 34 and the conductive housing electrode of implantable pulse generator 14). In a further example, implantable pulse generator 14 may deliver pacing pulses via pacing vector in which electrodes 32 and 34 together form the cathode (or anode) of the pacing vector and the housing electrode of implantable pulse generator 14 functions as the anode (or cathode) of the pacing vector. Implantable pulse generator 14 may generate and deliver the pacing pulses to provide bradycardia pacing or other pacing therapies or combination of pacing therapies, e.g., antitachycardia pacing (ATP) or post-shock pacing. In this manner, pacing therapy may be provided without entering the vasculature or the pericardium, and without being attached to heart 26.

Implantable pulse generator 14 may also sense electrical activity of heart 26 via one or more unipolar or bipolar sensing vectors formed via combinations of electrodes 32 and 34 and the housing electrode of implantable pulse generator 14. For example, implantable pulse generator 14 may sense electrical signals using a bipolar sensing vector between electrodes 32 and 34, via a unipolar sensing vector (e.g., between electrode 32 and the conductive housing electrode of implantable pulse generator 14 or between electrode 34 and the conductive housing electrode of implantable pulse generator 14), or a combination thereof. In some instances, implantable pulse generator 14 may deliver the pacing therapy based on the electrical signals sensed via the one or more of the sensing vectors of lead 18. Thus, implantable pulse generator 14 may deliver pacing therapy using pacing modes such as AAI, VVI, DDD, DDI, VAT, VDD, DVI, or other pacing mode that inhibit and/or trigger pacing based on sensed signals. In other instances, implantable pulse generator 14 may deliver pacing pulses independent of sensing, e.g., using asynchronous pacing modes such as AOO, VOO, DOO, or other mode with no sensing or with no inhibiting or triggering in response to sensing, e.g., AAO, VVO, or the like. Implantable pulse generator 14 may further provide pacing that is rate-responsive in addition to any of the modes described above.

Implantable pulse generator 14 may include a housing that forms a hermetic seal that protects components of implantable pulse generator 14. The housing of implantable pulse generator 14 may be formed of a conductive material, such as titanium. Implantable pulse generator 14 may also include a connector assembly (also referred to as a connector block or header) that includes electrical feedthroughs through which electrical connections are made between conductors within lead 18 and electronic components included within the housing. As will be described in further detail herein, housing may house one or more processors, memories, transmitters, receivers, sensors, sensing circuitry, therapy circuitry, power sources and other appropriate components. The housing of implantable pulse generator 14 is configured to be implanted in a patient, such as patient 12.

Lead 18 may further include one or more anchoring mechanisms that are positioned along the length of the lead body. The anchoring mechanisms may affix lead 18 to the loose connective tissue or other structures of the anterior mediastinum 36 to reduce movement of lead 18 from its desired location. For example, the lead 18 may be anchored at one or more locations situated between the distal lead end positioned within anterior mediastinum 36 of patient 12 and a point along the length of the portion of the lead body at or near the insertion point of the lead body into the anterior mediastinum 36. The one or more anchoring mechanism(s) may either engage bone, fascia, muscle or other tissue of patient 12 or may simply be wedged therein to affix the lead under the sternum to prevent excessive motion or dislodgment. Furthermore, it should be understood that various anchoring mechanisms described in this disclosure may additionally be utilized for delivery of a stimulation therapy as is known in the art.

The anchoring mechanisms may be integrated into the lead body. In such embodiments, a portion or segment of the lead body may be formed with materials that function to encase conductors and other elements internal to the lead while also anchoring the lead within the implant environment. In alternative embodiments, the anchoring mechanisms may be discrete elements formed in line with the lead body. In some embodiments, the discrete components may be provided in a fixedly-secured relationship to the lead body. In other embodiments, the anchoring mechanism may be detachedly coupled in a sliding relationship over the lead body. In addition or alternatively, the lead may be anchored through a suture that fixedly-secures the lead to the patient's musculature, tissue or bone at the xiphoid entry site. In some embodiments, the suture may be sewn through pre-formed suture holes to the patient.

The anchoring mechanisms may include a passive anchoring mechanism, an active anchoring mechanism or a combination of both. In one embodiment, the anchoring mechanism is coupled at a distal end of the lead body and may also function as an electrically active element. Examples of passive anchoring mechanisms include flanges, disks, pliant tines, flaps, porous structures such as a mesh-like element that facilitate tissue growth for engagement, bio-adhesive surfaces, and/or any other non-piercing elements. Examples of active anchoring mechanisms may include rigid tines, prongs, barbs, clips, screws, and/or other projecting elements that pierce and penetrate into tissue to anchor the lead. As another example of an active anchoring mechanism, the lead may be provided with a side helix for engaging tissue. In still further examples, lead 18 may be fixated via an electrically activated fixation, e.g., cautery, RF energy, or cryo to anchor lead 18 in place.

The various examples of the anchoring mechanisms may be deployable. As such, the anchoring mechanism assumes a first state during maneuvering of the lead (during which time the lead is disposed within a lumen of a delivery system) to the desired implant location. Subsequently, the anchoring mechanism assumes a second state following the release of the lead from the delivery system into the anterior mediastinum 36 to thereby anchor the distal end portion of the lead body relative to the adjacent tissue.

The examples illustrated in FIGS. 1A-C are exemplary in nature and should not be considered limiting of the techniques described in this disclosure. For instance, the configuration described above in FIGS. 1A-1C is directed to providing ventricular pacing via lead 18. In situations in which atrial pacing is desired in addition to or instead of ventricular pacing, lead 18 may be positioned further superior. A lead configured to deliver pacing pulses to both the atrium and ventricle may include more electrodes or still two electrodes with larger spacing between the electrodes. For example, the lead may have one or more electrodes located over a cardiac silhouette of the atrium as observed the AP fluoroscopic view of heart 26 and one or more electrodes located over a cardiac silhouette of the ventricle as observed in AP fluoroscopic view of heart 26. One such example is illustrated and described in more detail with respect to FIGS. 2A and 2B. A lead configured to deliver pacing pulses to only the atrium may, for example, have one or more electrodes located over a cardiac silhouette of the atrium as observed in the AP fluoroscopic view of heart 26. Again, the lead in this example could include one or more atrial electrodes that are implanted such that a therapy vector between the electrodes is substantially over the atrium and/or the therapy vector between one of the electrodes and the housing electrode is substantially across the atrium of heart 26. In some instances, two leads may be utilized with one being an atrial lead implanted such that the distal portion of the lead is substantially within the anterior mediastinum 36 such that the electrodes are located over a cardiac silhouette of the atrium as observed in the AP fluoroscopic view of heart 26 and the other being a ventricular lead being implanted such that the distal portion of the lead is substantially within the anterior mediastinum 36 such that the electrodes are located over a cardiac silhouette of the ventricle as observed in the AP fluoroscopic view of heart 26. One such example is illustrated and described in more detail with respect to FIGS. 3A and 3B.

In other examples, implantable pulse generator 14 and lead 18 may be implanted at other locations. For example, implantable pulse generator 14 may be implanted in a subcutaneous pocket in the right pectoral region. In this example, lead 18 may extend subcutaneously from the device toward the manubrium of sternum 22 to the desired location and bend or turn and extend inferior substantially within anterior mediastinum 36 from the manubrium of sternum 22 to the desired location. In yet another example, implantable pulse generator 14 may be placed abdominally.

In addition, it should be noted that system 10 may not be limited to treatment of a human patient. In alternative examples, system 10 may be implemented in non-human patients, e.g., primates, canines, equines, pigs, ovines, bovines and felines. These other animals may undergo clinical or research therapies that may benefit from the subject matter of this disclosure.

Although the description herein is in the context of pulse generator 14 providing pacing pulses to a heart, the techniques of this disclosure may also be used in the context of other implantable medical devices configured to provide electrical stimulation pulses to stimulate other nerves, skeletal muscles, diaphragmatic muscles, e.g., for various neurocardiac applications and/or for apnea or respiration therapy.

Figure 2A:
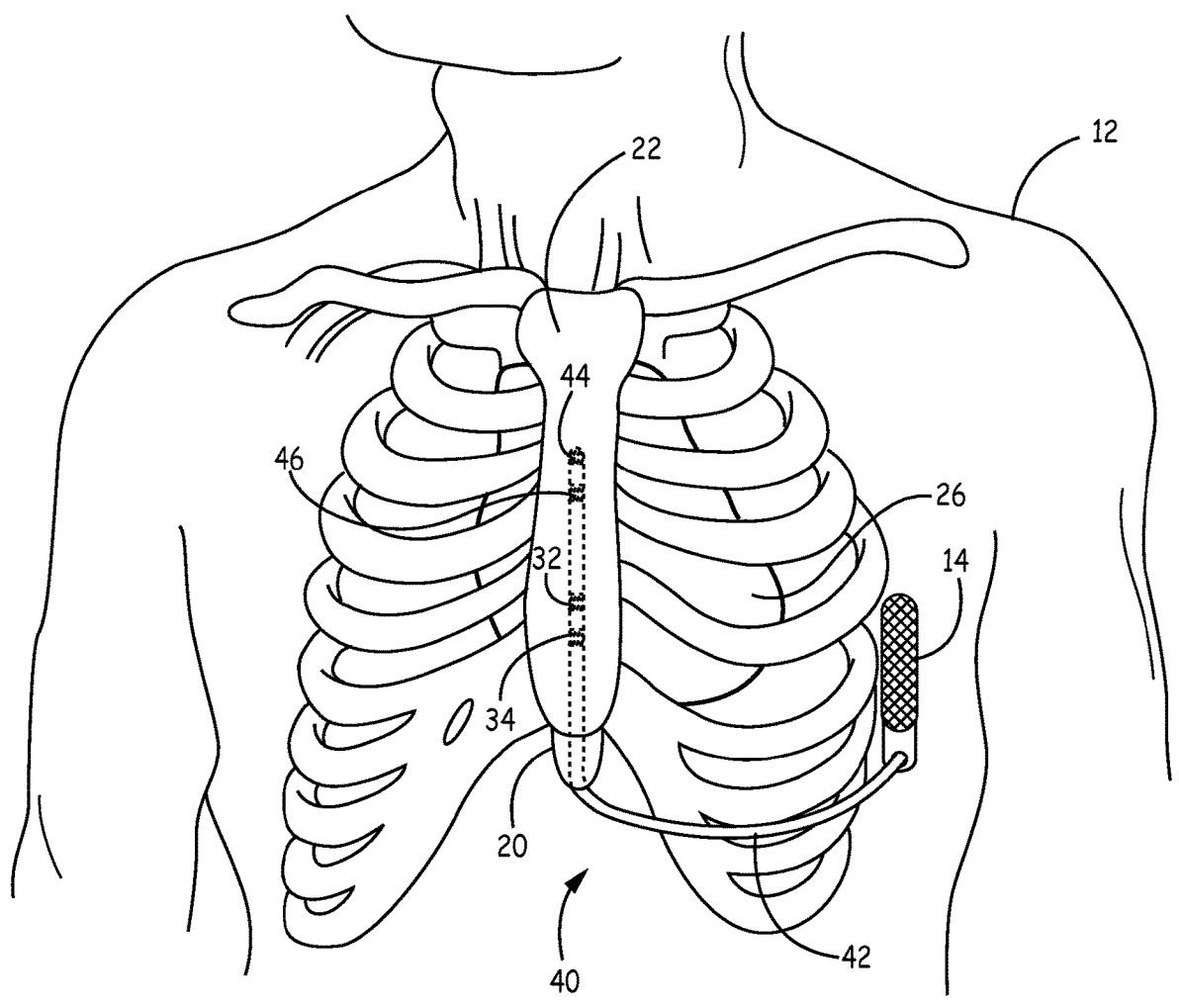
FIG. 2A is a front view of patient 12 implanted with implantable cardiac pacing system 40.
Figure 2B:
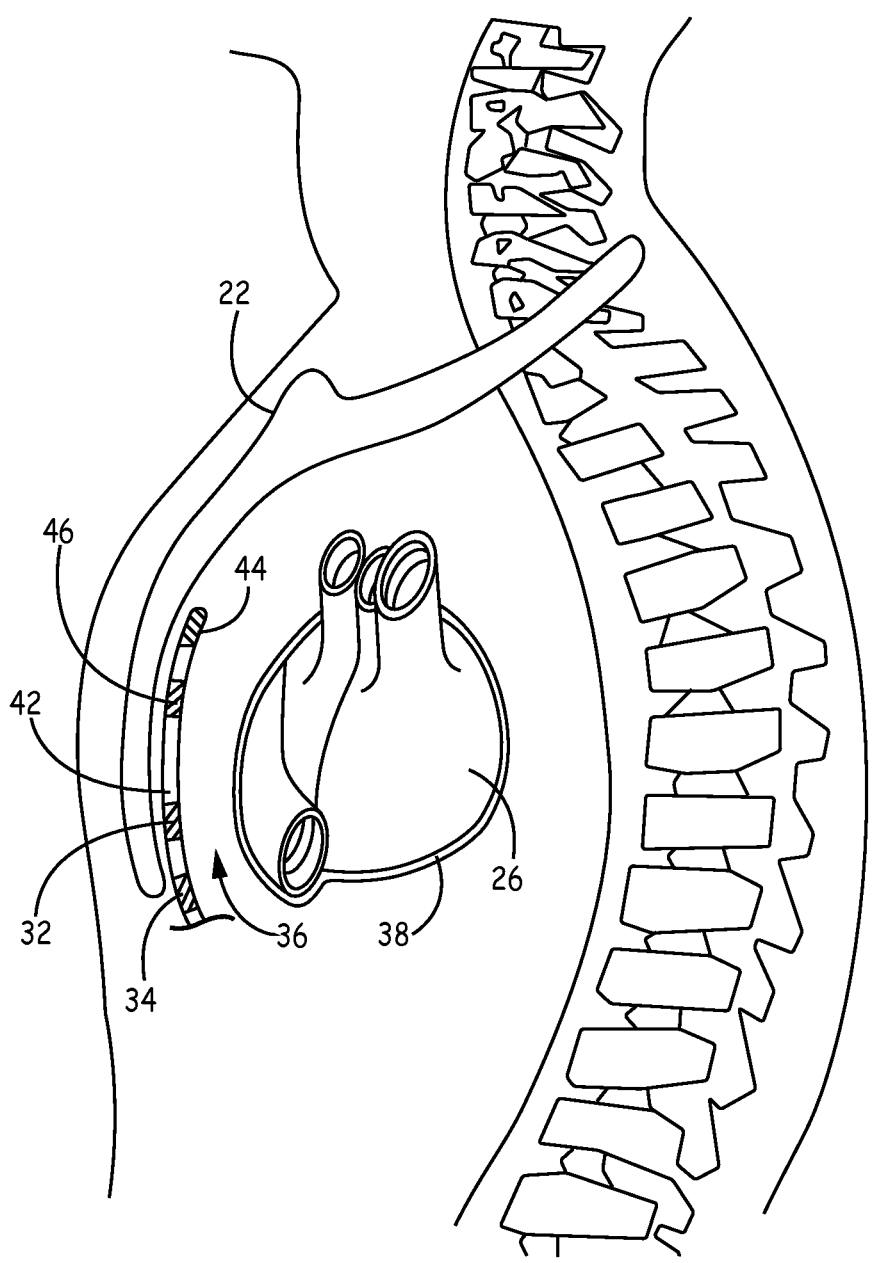
FIG. 2B is a side view of patient 12 with implantable cardiac pacing system 40.

FIGS. 2A and 2B are conceptual diagrams of patient 12 implanted with another example implantable cardiac pacing system 40. FIG. 2A is a front view of patient 12 implanted with implantable cardiac pacing system 40. FIG. 2B is a side view of patient 12 with implantable cardiac pacing system 40. Implantable cardiac pacing system 40 conforms substantially to implantable cardiac pacing system 10 of FIGS. 1A-1C, but pacing system 40 includes a lead 42 that includes electrodes 44 and 46 in addition to electrodes 32 and 34. Repetitive description of like numbered elements described in other embodiments is omitted for sake of brevity.

Lead 42 includes an elongated lead body having a proximal end that includes a connector configured to be connected to implantable pulse generator 14 and a distal portion that includes electrodes 32, 34, 44, and 46. Electrodes 44 and 46 conform substantially to electrodes 32 and 34. Therefore, description of electrodes 32 and 34 will not be repeated here, but is equally applicable to electrodes 44 and 46. In other embodiments, lead 42 may include more or fewer electrodes. Additionally, the elongated lead body may include the structure and/or function described above with respect to lead 18. The lead body of lead 42, for example, contains one or more elongated electrical conductors (not illustrated) that extend through the lead body from the connector at the proximal lead end to electrodes 32, 34, 44 and 46 located along the distal portion of lead 42. Lead 42 extends subcutaneously above the ribcage from implantable pulse generator 14 toward a center of the torso of patient 12 turns and extends superior underneath/below the sternum 22 substantially within anterior mediastinum 36. In other words, the distal portion of lead 42 extends along the posterior side of sternum 22 substantially within anterior mediastinum 36.

Lead 42 may be implanted substantially within the anterior mediastinum 36 such that implantable pulse generator 14 is capable of sensing electrical signals from and delivering electrical stimulation therapy to multiple chambers of heart 26. To this end, lead 42 may be implanted such that electrodes 32 and 34 are located near a ventricle of heart 26 and electrodes 44 and 46 are located near an atrium of heart 26. For instance, lead 42 may be implanted such that electrodes 32 and 34 are located over a cardiac silhouette of the ventricle as observed via an AP fluoroscopic view of heart 26 (as described in detail with respect to FIGS. 1A-1C) and electrodes 44 and 46 are located over a cardiac silhouette of the atrium as observed via the AP fluoroscopic view of heart 26.

For example, lead 42 may be implanted such that a unipolar therapy vector from electrode 44 to a housing electrode of implantable pulse generator 14 and/or a unipolar therapy vector from electrode 46 to the housing electrode of implantable pulse generator 14 are substantially across the atrium of heart 26. The therapy vector may be viewed as a line that extends from a point on electrode 44 or 46, e.g., center of electrode 44 or 46, to a point on the housing electrode of implantable pulse generator 14, e.g., center of the housing electrode. Alternatively or additionally, the spacing between electrodes 44 and 46 as well as the placement of lead 42 may be such that a bipolar therapy vector between electrode 44 and electrode 46 is centered or otherwise located over the atrium of heart 46. In other examples, pacing device 14 may sense electrical activity and/or delivery therapy to multiple chambers using therapy vectors formed using any combination of electrodes 32, 34, 44, and 46, and the housing electrode of pacing device 14. In this manner, pacing system 50 may provide multi-chamber pacing.

Figure 3A:
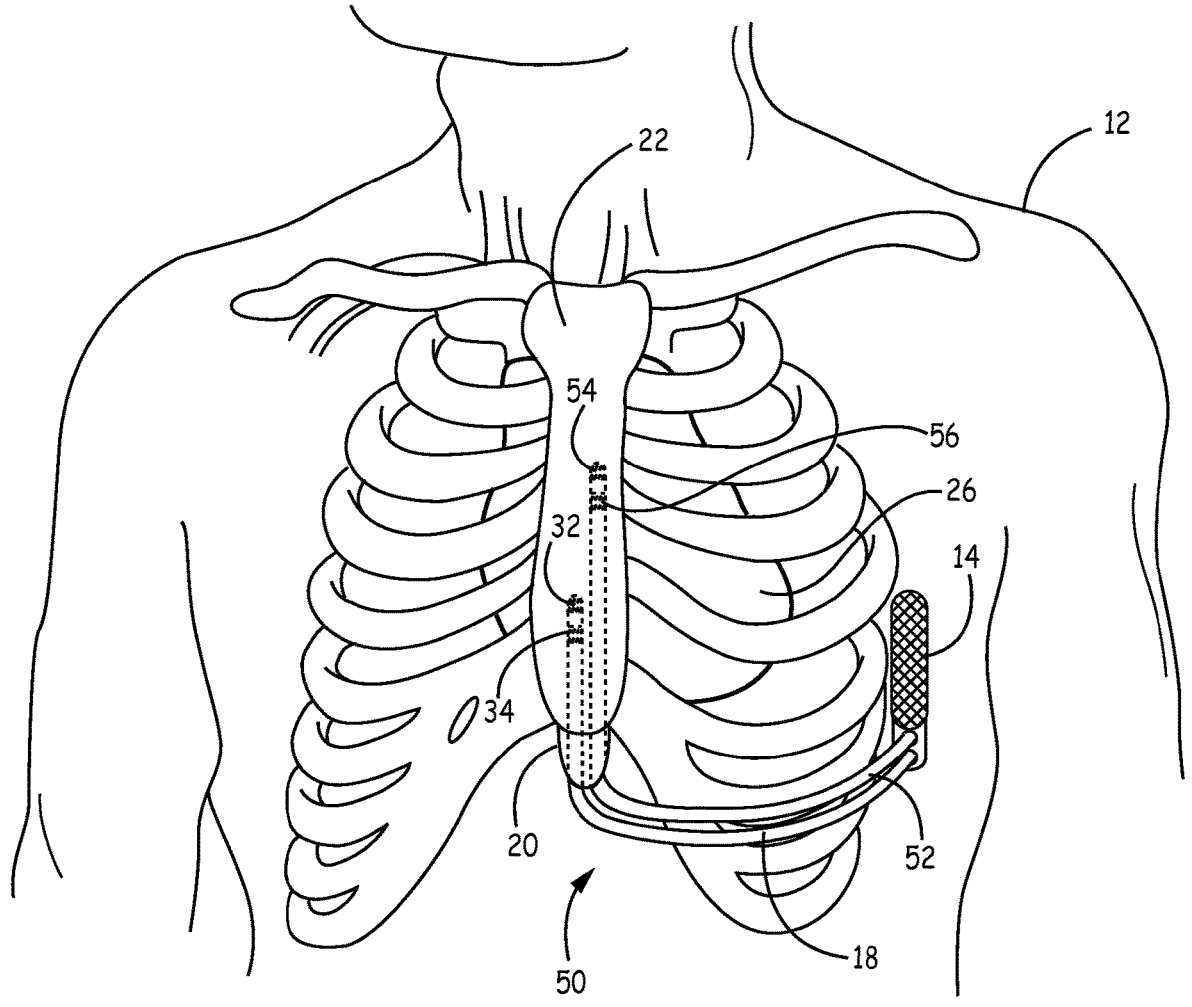
FIG. 3A is a front view of patient 12 implanted with implantable cardiac pacing system 50.
Figure 3B:
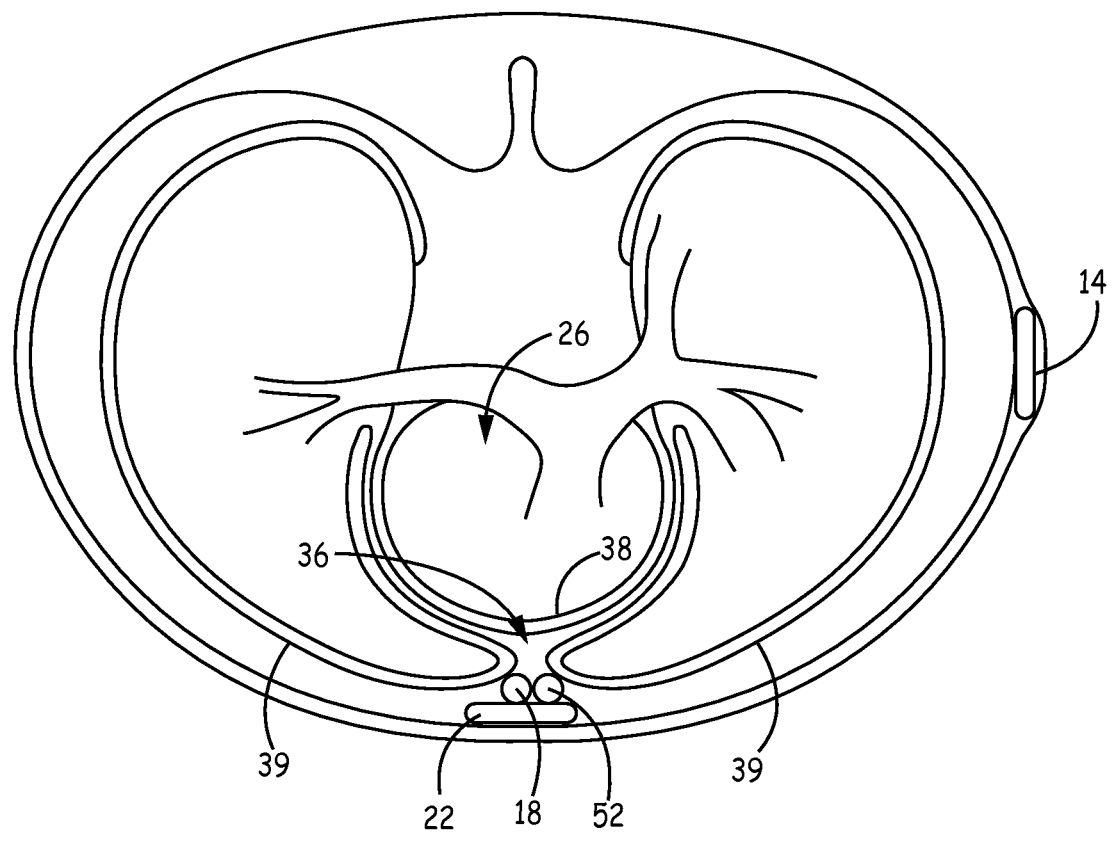
FIG. 3B is a transverse view of patient 12 with implantable cardiac pacing system 50.

FIGS. 3A and 3B are conceptual diagrams of a patient 12 implanted with another example implantable cardiac pacing system 50 that includes implantable pulse generator 14 coupled to leads 18 and 52. FIG. 3A is a front view of patient 12 implanted with implantable cardiac pacing system 50. FIG. 3B is a transverse view of patient 12 with implantable cardiac pacing system 50. Implantable cardiac pacing system 50 conforms substantially to pacing system 10 of FIGS. 1A-1C, except pacing system 50 includes an additional lead 52. Repetitive description of like numbered elements described in other embodiments is omitted for sake of brevity.

Lead 52 includes an elongated lead body having a proximal end that includes a connector configured to be connected to implantable pulse generator 14 and a distal portion that includes electrodes 54 and 56. Electrodes 44 and 46 conform substantially to electrodes 32 and 34. Therefore, description of electrodes 32 and 34 will not be repeated here, but is equally applicable to electrodes 44 and 46. In other instances, lead 52 may include more or fewer electrodes. Additionally, the elongated lead body of lead 52 contains one or more elongated electrical conductors (not illustrated) that extend through the lead body from the connector at the proximal lead end to electrodes 54 and 56 located along the distal portion of lead 52. Lead 52 extends subcutaneously above the ribcage from implantable pulse generator 14 toward a center of the torso of patient 12 turns and extends superior underneath/below the sternum 22 substantially within anterior mediastinum 36. In other words, the distal portion of lead 52 extends along the posterior side of sternum 22 substantially within anterior mediastinum 36.

As described in detail with respect to FIGS. 1A-1C, lead 18 is implanted substantially within the anterior mediastinum 36 such that the electrodes 32 and 34 are located near a ventricle of heart 26. Lead 52 may be implanted substantially within the anterior mediastinum 36 such that the electrodes 54 and 56 are located near an atrium of heart 26. For instance, lead 52 may be implanted such that electrodes 54 and/or 56 are located over a cardiac silhouette of the atria as observed via an AP fluoroscopic view of heart 26. For example, lead 52 may be implanted such that a unipolar therapy vector from electrode 54 to a housing electrode of implantable pulse generator 14 and/or a unipolar therapy vector from electrode 56 to the housing electrode of implantable pulse generator 14 are substantially across the atrium of heart 26. The therapy vector may be viewed as a line that extends from a point on electrode 54 or 56, e.g., center of electrode 54 or 56, to a point on the housing electrode of implantable pulse generator 14, e.g., center of the housing electrode. Alternatively or additionally, the spacing between electrodes 54 and 56 as well as the placement of lead 52 may be such that a bipolar therapy vector between electrode 54 and electrode 56 is centered or otherwise located over the atrium of heart 56. In this manner, pacing system 50 includes an atrial lead 52 and a ventricular lead 54. In other instances, pacing system 50 may sense electrical activity from and/or delivery therapy to heart 26 using electrode vectors formed using any combination of electrodes 32, 34, 54, and 56, and the housing electrode of pacing device 14. In this manner, pacing system 50 may provide multi-chamber pacing.

Figure 4:
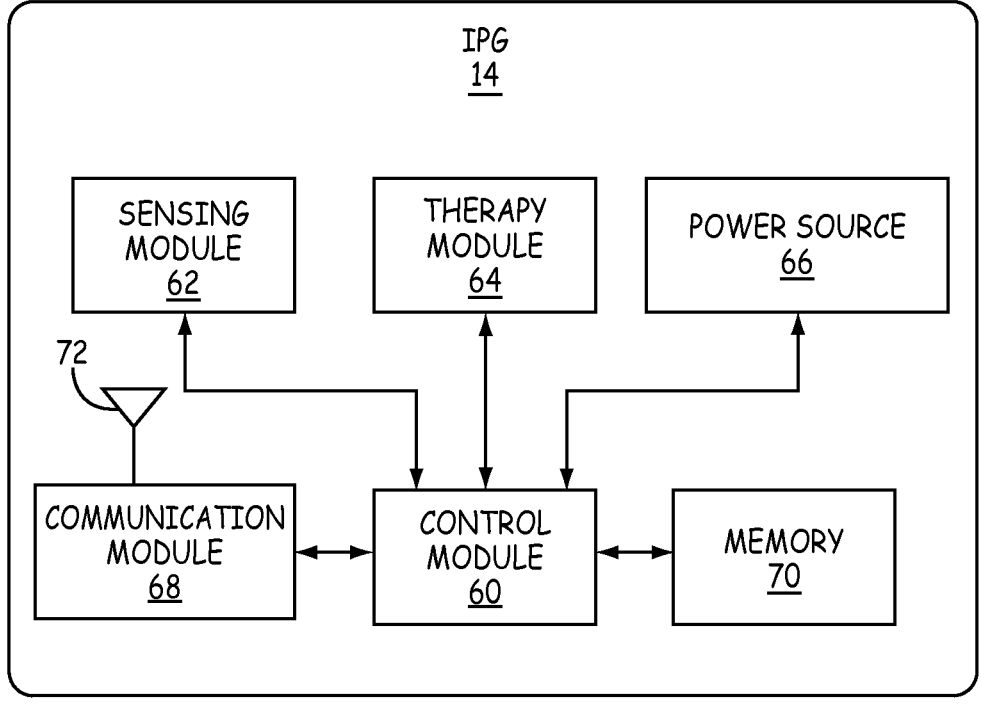
FIG. 4 is a functional block diagram of an example configuration of electronic components of an example implantable pulse generator 14.

FIG. 4 is a functional block diagram of an example configuration of electronic components of an example implantable pulse generator 14. Implantable pulse generator 14 includes a control module 60, sensing module 62, therapy module 64, communication module 68, and memory 70. The electronic components may receive power from a power source 66, which may be a rechargeable or non-rechargeable battery. In other embodiments, implantable pulse generator 14 may include more or fewer electronic components. The described modules may be implemented together on a common hardware component or separately as discrete but interoperable hardware, firmware, or software components. Depiction of different features as modules is intended to highlight different functional aspects and does not necessarily imply that such modules must be realized by separate hardware, firmware, or software components. Rather, functionality associated with one or more modules may be performed by separate hardware, firmware, or software components, or integrated within common or separate hardware or software components.

Sensing module 62 is electrically coupled to some or all of electrodes 32, 34, 44, 46, 54, or 56 via the conductors of leads 18, 42, or 52 and one or more electrical feedthroughs, or to the housing electrode via conductors internal to the housing of implantable pulse generator 14. Sensing module 62 is configured to obtain signals sensed via one or more sensing vectors formed by combinations of electrodes 32, 34, 44, 46, 54, or 56, and the housing electrode of implantable pulse generator 14 and process the obtained signals.

The components of sensing module 62 may be analog components, digital components or a combination thereof. Sensing module 62 may, for example, include one or more sense amplifiers, filters, rectifiers, threshold detectors, analog-to-digital converters (ADCs) or the like. Sensing module 62 may convert the sensed signals to digital form and provide the digital signals to control module 60 for processing or analysis. For example, sensing module 62 may amplify signals from the sensing electrodes and convert the amplified signals to multi-bit digital signals by an ADC. Sensing module 62 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 60.

Control module 60 may process the signals from sensing module 62 to monitor electrical activity of heart 26 of patient 12. Control module 60 may store signals obtained by sensing module 62 as well as any generated EGM waveforms, marker channel data or other data derived based on the sensed signals in memory 70. Control module 60 may analyze the EGM waveforms and/or marker channel data to deliver pacing pulses as a function of the sensed cardiac events, e.g., pacing pulses triggered or inhibited based on the detection or lack of detection of intrinsic cardiac activity. In some instances, control module 60 may also detect cardiac events, such as tachyarrhythmia, based on the sensed electrical signals.

Therapy module 64 is configured to generate and deliver electrical stimulation therapy to heart 26. Therapy module 64 may include one or more pulse generators, capacitors, and/or other components capable of generating and/or storing energy to deliver as pacing therapy. Control module 60 may control therapy module 64 to generate electrical stimulation therapy and deliver the generated therapy to heart 26 via one or more therapy vectors formed using combinations of electrodes 32, 34, 44, 46, 54, or 56 and the housing electrode of implantable pulse generator 14 according to one or more therapy programs, which may be stored in memory 70. Control module 60 controls therapy module 64 to generate electrical stimulation therapy with the amplitudes, pulse widths, timing, frequencies, electrode combinations or electrode configurations specified by a selected therapy program.

Therapy module 64 may generate and deliver pacing pulses with any of a number of shapes, amplitudes, pulse widths, or other characteristic to capture heart 26. For example, the pacing pulses may be monophasic, biphasic, or multi-phasic (e.g., more than two phases). The pacing thresholds of heart 26 when delivering pacing pulses from the anterior mediastinum using leads 18, 42, and/or 52 may depend upon a number of factors, including location, type, size, orientation, and/or spacing of the electrodes, location of implantable pulse generator 14 relative to the electrodes, physical abnormalities of heart 26 (e.g., pericardial adhesions or myocardial infarctions), or other factor(s).

The increased distance from electrodes 32, 34, 44, 46, 54, or 56 to the heart tissue may result in heart 26 having increased pacing thresholds compared to transvenous pacing thresholds. To this end, therapy module 64 may be configured to generate and deliver pacing pulses having larger amplitudes and/or pulse widths than conventionally required to obtain capture via transvenously implanted lead or a lead attached to heart 26. In one example, therapy module 64 may generate and deliver pacing pulses having amplitudes of less than or equal to 8 volts and pulse widths between 0.5-3.0 milliseconds. In another example, therapy module 64 may generate and deliver pacing pulses having amplitudes of between 5 and 10 volts and pulse widths between approximately 3.0 milliseconds and 10.0 milliseconds. In another example, therapy module 64 may generate and deliver pacing pulses having pulse widths between approximately 2.0 milliseconds and 8.0 milliseconds. In a further example, therapy module 64 may generate and deliver pacing pulses having pulse widths between approximately 0.5 milliseconds and 20.0 milliseconds. In another example, therapy module 64 may generate and deliver pacing pulses having pulse widths between approximately 1.5 milliseconds and 20.0 milliseconds.

In some cases, therapy module 64 may generate pacing pulses having longer pulse durations than conventional transvenous pacing pulses to achieve lower energy consumption. For example, therapy module 64 may be configured to generate and deliver pacing pulses having pulse widths or durations of greater than two (2) milliseconds. In another example, therapy module 64 may be configured to generate and deliver pacing pulses having pulse widths or durations of between greater than two (2) milliseconds and less than or equal to three (3) milliseconds. In another example, therapy module 64 may be configured to generate and deliver pacing pulses having pulse widths or durations of greater than or equal to three (3) milliseconds. In another example, therapy module 64 may be configured to generate and deliver pacing pulses having pulse widths or durations of greater than or equal to five (5) milliseconds. In another example, therapy module 64 may be configured to generate and deliver pacing pulses having pulse widths or durations of greater than or equal to ten (10) milliseconds. In a further example, therapy module 64 may be configured to generate and deliver pacing pulses having pulse widths between approximately 3-10 milliseconds. In a further example, therapy module 64 may be configured to generate and deliver pacing pulses having pulse widths or durations of greater than or equal to fifteen (15) milliseconds. In yet another example, therapy module 64 may be configured to generate and deliver pacing pulses having pulse widths or durations of greater than or equal to twenty (20) milliseconds.

Depending on the pulse widths, therapy module 64 may be configured to generate and deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. These pulse amplitudes may be combined with any of the pulse widths/durations described above. Reducing the amplitude of pacing pulses delivered by implantable pulse generator 14 may reduce the likelihood of extra-cardiac stimulation. Some experimental results are provided later illustrating some example combinations of pacing amplitudes and widths.

In some instances, implantable pulse generator 14 may be configurable to be used with lead 18, 42, or 52 implanted substantially within the anterior mediastinum 36 or a lead located within heart 26 or placed epicardially or intrapericardial. To this end, implantable pulse generator 14 may include multiple pacing modes with pacing parameters corresponding to the location from which the pacing pulses will be delivered. Implantable pulse generator 14 may include a first pacing mode (e.g., a substernal pacing mode) in which pacemaker is configured to generate and deliver pacing pulses having amplitudes and durations for pacing from the substernal space and a second pacing mode (e.g., a "normal" pacing mode) in which pacemaker is configured to generate and deliver pacing pulses having amplitudes and durations for pacing from conventional pacing locations, e.g., inside heart 26 or epicardially. Implantable pulse generator 14 may deliver pacing pulses having substantially the same amplitudes in the substernal pacing mode and normal pacing mode, but the pacing pulses in the substernal pacing mode may have longer pulse widths or durations. As described above, in some instances implantable pulse generator 14 may generate and deliver pacing pulses that have pulse widths of up to 20 milliseconds. Alternatively, implantable pulse generator 14 may deliver pacing pulses having different amplitudes and pulse widths in the substernal pacing mode than the normal pacing mode. For example, implantable pulse generator 14 may deliver pacing pulses have larger amplitudes and durations in the substernal pacing mode than in the normal pacing mode. In another example, implantable pulse generator 14 may deliver pacing pulses having smaller amplitudes and longer durations in the substernal pacing mode than in the normal pacing mode in an attempt to reduce extra-cardiac stimulation. When implanted, a programmer or other external instrument may provide a selection to the physician to select the particular pacing mode.

Communication module 68 includes any suitable hardware, firmware, software or any combination thereof for communicating with another device, such as a clinician programmer, a patient monitoring device, or the like. For example, communication module 68 may include appropriate modulation, demodulation, frequency conversion, filtering, and amplifier components for transmission and reception of data with the aid of antenna 72. Antenna 72 may be located within connector block of implantable pulse generator 14 or within housing implantable pulse generator 14.

The various modules of implantable pulse generator 14 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 70 may include computer-readable instructions that, when executed by control module 60 or other component of implantable pulse generator 14, cause one or more components of implantable pulse generator 14 to perform various functions attributed to those components in this disclosure. Memory 70 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

EXPERIMENTS

Three acute procedures were performed using pigs, with the animals in a dorsal recumbency. An incision was made near the xiphoid process and a Model 4194 lead was delivered to the substernal/retrosternal space using a 6996T tunneling tool and sheath. An active can emulator (ACE) was placed in a subcutaneous pocket on either the right chest (first acute experiment) or the left midaxillary (second and third acute experiments). Various pacing configurations were tried and different pieces of equipment were used as the source of stimulation. Multiple pulse widths were used in delivering the pacing pulse. Across experiments, several different substernal/retro sternal lead electrode locations were utilized.

In the second and third experiments the impact of lead location on electrical performance was investigated by moving the lead to several locations under the sternum and collecting data to generate strength-duration curves at each location.

In all three acute experiments, the substernal/retrosternal lead was placed and electrical data collected. The lead was moved intentionally many times across experiments to better understand the location best suited to capturing the heart at low pacing thresholds, with different locations and parameters tried until pacing capability was gained and lost. A range of thresholds based on location and pacing configuration was recorded. For this reason, the lowest threshold result for each acute experiment is reported, as are strength-duration curves showing the range of pacing values obtained from suitable pacing locations. In all cases, it was determined that positioning the substernal/retrosternal pacing electrode approximately over the ventricle of the cardiac silhouette provided best results.

Experiment 1

In the first acute study, a MEDTRONIC ATTAIN bipolar OTW 4194 lead (referred to herein as "the 4194 lead") was implanted substernally, and two active can emulators were positioned, one in the right dorsal lateral region (ACE1) and one on the right midaxillary (ACE2). The 4194 lead was placed directly below the sternum, in the mediastinum, with the lead tip and body running parallel to the length of the sternum. Various pacing configurations were tried and electrical data collected.

The smallest threshold observed was 0.8 volts, obtained when pacing from the tip of the substernal/retrosternal 4194 lead to ACE1 (10 ms pulse width and Frederick Heir instrument as the source of stimulation). It was possible to capture using a smaller pulse width, though threshold increased as the pulse width shortened (1.5V at 2 ms in this same configuration with the Frederick Heir Stimulator. Many additional low thresholds (1-2 volts) were obtained with different pacing configurations and pulse durations.

FIG. 5 illustrates a strength-duration curve showing the capture thresholds obtained at various pulse widths during the first acute study. Note that all configurations paced from either the tip or the ring of the substernally implanted 4194 lead (−) to one of the two active can emulators (+). In one instance, a large spade electrode (instead of a Model 4194 lead) was used as the substernal/retrosternal electrode, as noted in the legend of.

As shown, several pacing configurations and parameters were tried. Across the configurations reported in the graph above, threshold values ranged from 0.8 volts to 5.0 volts, with threshold generally increasing as pulse width was shortened. In a few instances, the threshold at 1.5 ms pulse width was smaller than the threshold at 2.0 ms. It should be noted that the threshold value obtained at 1.5 ms was always recorded using the Medtronic 2290 analyzer as the stimulation source, whereas all other threshold measurements for the first acute experiment (at pulse widths of 2, 10, 15 and 20 mms) were obtained using a Frederick Heir instrument as the source of stimulation. Differences in these two instruments may account for the difference in threshold values at similar pulse widths (1.5 mms and 2 mms).

In general, the first acute experiment demonstrated the feasibility of substernal/retrosternal pacing by producing small capture thresholds (average=2.5±1.2 volts), using several different pacing configurations and parameters.

Experiment 2

A second acute experiment was conducted. In the second acute, however, the animal presented with pericardial adhesions to the sternum. Because of the pericardial adhesion, the ventricular surface of the cardiac silhouette was rotated away from the sternum—an anatomical difference that may have resulted in higher thresholds throughout this experiment.

As in the previous acute experiment, a Model 4194 lead was placed under the sternum. An active can emulator was placed on the left midaxillary. The tip to ring section of the 4194 was positioned over the cardiac silhouette of the ventricle, as observed by fluoroscopy, and this position is notated "Position A" on the strength-duration graph illustrated in FIG. 6. The lead eventually migrated a very short distance closer to the xiphoid process during stimulation (still under the sternum) to reach "Position B," and additional electrical measurements were obtained successfully from this position as well.

The smallest threshold observed in the second acute experiment was 7V, obtained when pacing from the substernal/retrosternal 4194 ring electrode (−) to an ACE (+) on the left midaxillary in the first lead position (5 ms, 15 ms and 20 ms pulse widths, Frederick Heir stimulator). Additionally, thresholds of 8 and 9 volts were obtained with the lead in the second anatomical position, both from 4194 tip to ACE (unipolar) and 4194 tip to ring (bipolar) configurations at multiple pulse widths. The two lines that appear to run off the chart were instances of no capture.

All of the electrical values reported in FIG. 6 were collected with the Frederick Heir instrument as the stimulation source. Extra-cardiac stimulation was observed with many of the electrical measurements obtained in a unipolar pacing configuration. No obvious extra-cardiac stimulation was observed when pacing in a bipolar configuration (4194 tip to ring), though a low level of stimulation could be felt with a hand on the animal's chest.

Experiment 3

A third and final acute experiment was conducted demonstrating the feasibility of substernal/retrosternal pacing. As in the previous two acute experiments, a 4194 lead was placed under the sternum. An active can emulator was placed on the left midaxillary. In this experiment, the substernal/retrosternal 4194 lead was intentionally positioned so that the lead tip was initially near the second rib, far above the cardiac silhouette of the ventricle. The lead tip was then pulled back (toward the xiphoid process) one rib space at a time, collecting electrical data at each position. As in previous experiments, low capture thresholds were obtained when the pacing electrodes were approximately positioned over the ventricular surface of the cardiac silhouette, as observed via fluoroscopy. When the lead tip was not over the ventricular surface of the cardiac silhouette, "no capture" was often the result.

As in previous experiments, pacing was performed from either the tip or the ring of the substernal/retrosternal 4194 lead (−) to the ACE (+) on the left midaxillary. However, in this acute experiment, a subcutaneous ICD lead was also positioned in its subcutaneous arrangement (as illustrated and described in FIGS. 1A-C). In some instances, the pacing configuration was from either the tip or the ring of the substernal/retrosternal 4194 lead (−) to either the ring or the coil of the subcutaneous ICD lead (+), so that the ICD lead and not the ACE was the indifferent electrode.

The smallest threshold observed across the experiment was 0.8V, obtained when pacing from the substernal/retrosternal 4194 tip electrode (−) to an ACE (+) on the left midaxillary when the lead was positioned such that the lead tip electrode was approximately under the sixth rib (20 ms pulse width and Frederick Heir stimulator). Many additional low thresholds were obtained with different pacing configurations, shorter pulse durations and different lead positions, again demonstrating the feasibility of substernal/retrosternal pacing. Obvious extra-cardiac stimulation generally was not observed with lower threshold measurements (at longer pulse durations) but was observed at higher thresholds.

The strength duration curves for lead positions 3-5 are presented in FIGS. 5-7, with individual graphs for each location due to the breadth of electrical data collected. Measurements made with the 2290 analyzer as the source of stimulation are noted. Other electrical measurements were made with the Frederick Heir instrument as the stimulation source.

FIG. 7 illustrates the strength-duration curve of electrical data from the third acute experiment when the 4194 lead tip was positioned under the sternum at the location of the $4^{th}$ rib. Several therapy vectors resulted in low pacing thresholds, generally when pulse widths were quite long. At shorter pulse widths, threshold increased.

FIG. 8 illustrates the strength-duration curve of electrical data from the third acute experiment when the 4194 lead tip was positioned under the sternum at the location of the $5^{th}$ rib. The two lines that appear to run off the chart at 0.2 ms were instances of no capture. FIG. 8 demonstrates the position dependence of the substernal/retrosternal lead. Thresholds were higher overall in this anatomical location (the lead tip near the $5^{th}$ rib), though capture was still possible and in the 4194 ring (−) to ACE (+) configuration, moderately low (2 volts at 20 ms). There generally was no significant extra-cardiac stimulation observed except with pulse widths of 0.2 ms and 0.5 ms in the 4194 tip (−) to ACE (+) configuration and in the unipolar configuration going from the 4194 tip (−) to the coil of the subcutaneous ICD lead at pulse widths of 1.5 ms and shorter, all of which resulted in the highest recorded threshold readings in this lead position.

Figure 9:
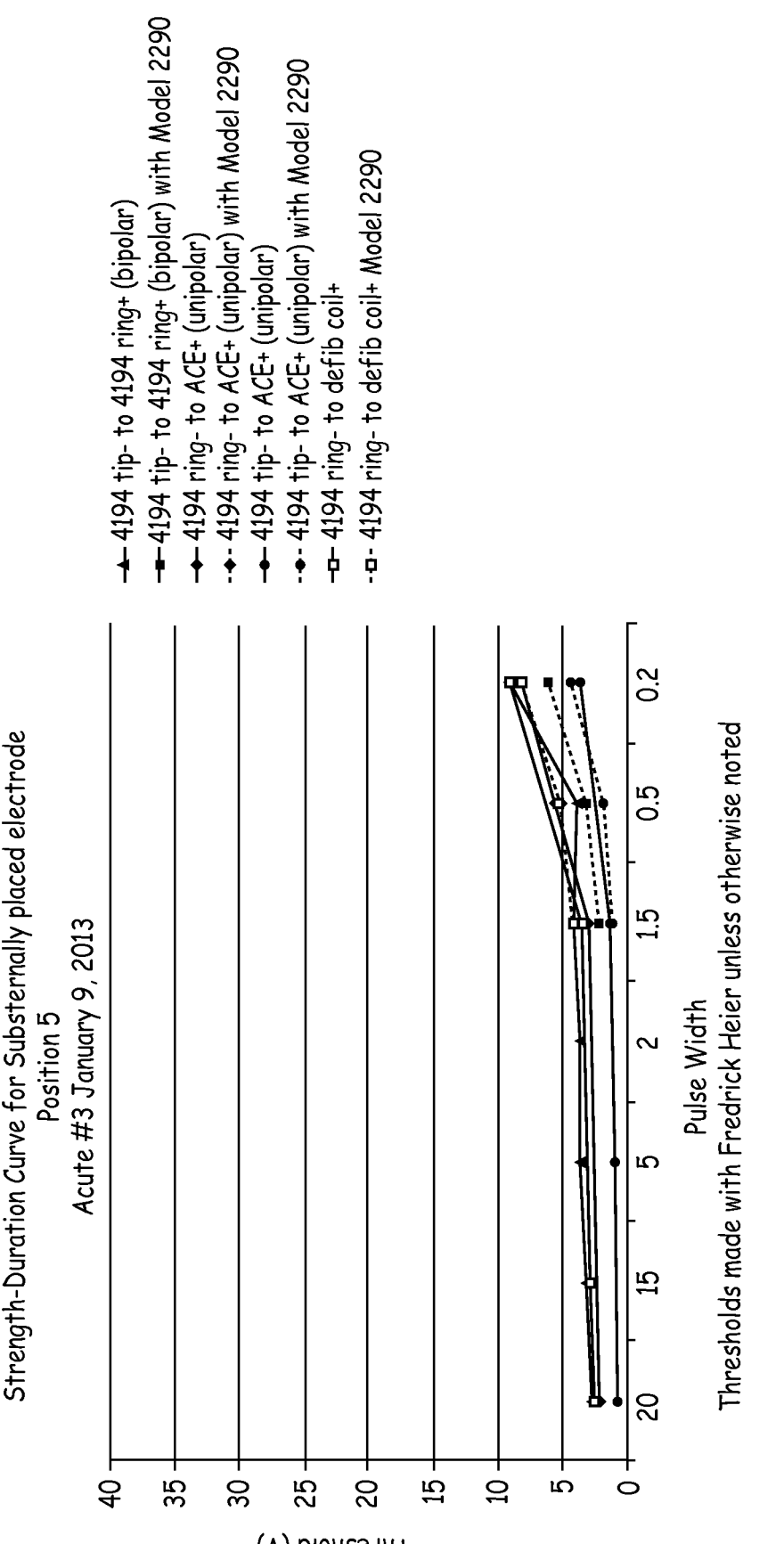
FIG. 9 is a graph illustrating strength-duration curves of electrical data from a third acute experiment.

FIG. 9 illustrates the strength-duration curve of electrical data from the third acute experiment when the 4194 lead tip was positioned under the sternum at the location of the $6^{th}$ rib. FIG. 9 shows the position dependence of the substernal/retrosternal electrode. When the pacing electrode is optimally located over the ventricular surface of the cardiac silhouette (as observed via fluoroscopy), pacing threshold is low. Low thresholds were very repeatable in this anatomical location, even at shorter pulse durations and in many different pacing configurations. Extra-cardiac stimulation generally was not apparent at low thresholds and longer pulse durations throughout this experiment.

All three acute experiments demonstrated the feasibility of pacing from a substernal/retrosternal electrode location. The lowest threshold results across the three acute procedures were 0.8 volts, 7 volts and 0.8 volts, respectively, with the second acute procedure involving an anatomical difference (pericardial adhesions) that tipped the ventricular surface of the heart away from its normal orientation with the sternum, resulting in higher pacing thresholds. However, for the purposes of anti-tachycardia pacing, conventional devices typically default to maximum output (8V at 1.5 ms) for ATP therapy delivery. Given this, even the 7V threshold obtained in the second acute experiment could be satisfactory for ATP therapy.

The ability to capture the heart at low pacing thresholds was dependent upon electrode position. As observed through these experiments, the substernal/retrosternal pacing electrode provide the best outcomes when positioned approximately over the ventricular surface of the cardiac silhouette, which is easily observed via fluoroscopy and encompasses a reasonably large target area for lead placement. In the third acute experiment, for example, capture was achieved at three separate positions, with the lead tip at approximately ribs 4, 5 and 6, all of which were near the ventricular surface of the cardiac silhouette.

Pacing thresholds increased with shorter pulse durations. In many instances, however, low pacing thresholds were obtained even at short pulse widths, especially when the substernal/retrosternal pacing electrode was positioned over the ventricular surface of the cardiac silhouette. In other instances, longer pulse durations (10-20 ms) were necessary to obtain capture or to achieve lower capture thresholds.

Across experiments, it was possible to pace from the substernal/retrosternal lead to an active can emulator positioned near the animal's side (unipolar) and also from the substernal/retrosternal lead to a subcutaneous ICD lead (unipolar). If a subcutaneous ICD system incorporated a lead, placed substernally, for the purpose of anti-tachycardia pacing, both of the aforementioned unipolar pacing configurations would be available for a physician to choose from.

These experiments also demonstrated the ability to pace in a bipolar configuration entirely under the sternum (4194 tip (−) to 4194 ring (+), substernally), indicating that either a bipolar lead positioned under the sternum might be used for anti-tachycardia pacing purposes.

Overall, the results of these acute experiments demonstrate the ability to pace the heart from a substernal/retrosternal location, with the lead not entering the vasculature or the pericardial space, nor making intimate contact with the heart. The low threshold values obtained when pacing from a substernal/retrosternal lead location in these acute experiments suggest that pain-free pacing for the purpose of anti-tachycardia pacing in a subcutaneous ICD system is within reach.

In some instances, electrodes 32 and 34 of lead 16 (or electrodes of leadless pacing device 50) may be shaped, oriented, designed or otherwise configured to reduce extra-cardiac stimulation. For example, electrodes 28 and 30 of lead 16 (or electrodes of leadless pacing device 50) may be shaped, oriented, designed or otherwise configured to focus, direct or point electrodes 28 and 30 toward heart 26. In this manner, pacing pulses delivered via lead 16 are directed toward heart 26 and not outward toward skeletal muscle. For example, electrodes 28 and 30 of lead 16 (or electrodes of leadless pacing device 50) may be partially coated or masked with a polymer (e.g., polyurethane) or another coating material (e.g., tantalum pentoxide) on one side or in different regions so as to direct the pacing signal toward heart 26 and not outward toward skeletal muscle.

Various examples have been described. These and other examples are within the scope of the following claims.

The invention claimed is:

1. A cardiac pacing system comprising:
  a pulse generator configured to provide cardiac pacing therapy;
  an implantable medical electrical lead that includes:
    a lead body having a proximal end and a distal portion;
    a connector configured to couple to the pulse generator at the proximal end of the lead body; and
    a plurality of electrodes on the distal portion of the lead body,
  wherein the distal portion of the lead body of the lead is configured to be positioned within the substernal space of the patient and the pulse generator is configured to deliver pacing pulses to an atrium of a heart of the patient using at least a first pair of electrodes of the plurality of electrodes and deliver pacing pulses to a ventricle of the heart of the patient via at least a second pair of electrodes of the plurality of electrodes, the first pair of electrodes and the second pair of electrodes being electrically coupled to a therapy circuitry of the pulse generator, the first pair of electrodes and the second pair of electrodes being positioned on the distal portion of the lead body that is configured to be positioned within the substernal space, the first pair of electrodes being spaced apart from the second pair of electrodes such that the first pair of electrodes are configured to deliver pacing pulses to the atrium of the heart of the patient and the second pair of electrodes are configured to deliver pacing pulses to the ventricle of the heart of the patient, wherein a distance between the first pair electrodes and the second pair of electrodes is greater than a distance between each electrode of the first pair of electrodes.

2. The system of claim 1, wherein the pulse generator is configured to provide one of bradycardia pacing, antitachy-cardia (ATP) pacing, and post-shock pacing to the patient via the lead.

3. The system of claim 1, wherein the distal portion of the lead is configured to be positioned within the substernal space such that the second pair of electrodes-is located over a cardiac silhouette of the ventricle of the heart as observed via an anterior-posterior (AP) fluoroscopic view of the heart or the first pair of electrodes-is located over a cardiac silhouette of the atrium of the heart as observed via an anterior-posterior (AP) fluoroscopic view of the heart.

4. The system of claim 1,
  wherein the first pair of electrodes is located along the lead body such that when the distal portion of the lead body is positioned within the substernal space, the first pair of electrodes-is located over a cardiac silhouette of the atrium of the heart as observed via an anterior-posterior (AP) fluoroscopic view of the heart to pace the atrium of the heart via the delivery of the pacing pulses, and
  wherein the second pair of electrodes is located along the lead body such that when the distal portion of the lead body is positioned within the substernal space, the second pair of electrodes-is located over a cardiac silhouette of the ventricle of the heart as observed via the AP fluoroscopic view of the heart to pace the ventricle of the heart via the delivery of the pacing pulses.

5. The system of claim 1, wherein the pulse generator is configured to deliver pacing pulses having pulse widths greater than or equal to two (2) milliseconds.

6. The system of claim 1, wherein the pulse generator is configured to deliver pacing pulses having pulse widths between two (2) and three (3) milliseconds.

7. The system of claim 1, wherein the pulse generator is configured to deliver pacing pulses having pulse widths between approximately one and a half (1.5) milliseconds and twenty (20) milliseconds.

8. The system of claim 1, wherein the pulse generator is configured to deliver pacing pulses having pulse widths greater than two (2) milliseconds and less than eight (8) milliseconds.

9. The system of claim 1, wherein the pulse generator is configured to deliver pacing pulses having pulse amplitudes between approximately one (1) and twenty (20) volts.

10. The system of claim 1, wherein the pulse generator includes a conductive housing that functions as an electrode and the pulse generator is configured to deliver pacing pulses between the plurality of electrodes on the lead and the electrode formed by the conductive housing.

11. The system of claim 1, wherein the distal portion of the lead body of the lead is configured to be positioned within the substernal space such that at least a portion of the distal portion is underneath a ribcage of the patient.

12. The system of claim 1, wherein the distal portion of the lead body of the lead is configured to be positioned within the substernal space such that at least a portion of the distal portion is between a ribcage of the patient and a pericardium of the patient.

13. A method comprising:
  generating one or more pacing pulses with a pulse generator; and
  delivering the one or more pacing pulses via a plurality of electrodes including at least a first pair of electrodes and a second pair of electrodes of an implantable medical electrical lead to a heart of the patient the implantable medical electrical lead including:
    a lead body having a proximal end and a distal portion; and
    the first pair of electrodes and the second pair of electrodes on the distal portion of the lead body, the first pair of electrodes being spaced apart from the second pair of electrodes such that the first pair of electrodes are configured to deliver pacing pulses to the atrium of the heart of the patient and the second pair of electrodes are configured to deliver pacing pulses to the ventricle of the heart of the patient, wherein a distance between the first pair electrodes and the second pair of electrodes is greater than a distance between each electrode of the first pair of electrodes, wherein, during the delivery of the pacing pulses, the distal portion of the lead body of the lead is positioned within the substernal space of the patient such that the plurality of electrodes are physically isolated from a pericardium of the patient.

14. The method of claim 13, wherein, during the delivery of the pacing pulses, the distal portion of the lead body of the lead is positioned within the substernal space such that at least a portion of the lead body is underneath a ribcage of the patient.

15. The method of claim 13, wherein, during the delivery of the pacing pulses, the distal portion of the lead body of the lead is positioned within the substernal space such that at least a portion of the lead body is between a ribcage of the patient and a pericardium of the patient.

16. The method of claim 13, wherein, during the delivery of the pacing pulses, the distal portion of the lead body of the lead is positioned within the substernal space such that at least a portion of the lead body is offset laterally from a center of a sternum of the patient.

17. The method of claim 13 further comprising:

anchoring, via one or more anchoring mechanisms positioned along the lead body, the lead body to loose connective tissue or structures of the anterior mediastinum such that the plurality of electrodes are physically isolated from the pericardium of the patient.

* * * * *